US011827917B1

(12) United States Patent
Reardon et al.

(10) Patent No.: US 11,827,917 B1
(45) Date of Patent: Nov. 28, 2023

(54) METHODS FOR THE CONVERSION OF FERMENTABLE SUGARS TO ETHANOL

(71) Applicants: Kenneth F. Reardon, Fort Collins, CO (US); Xingfeng Huang, Fort Collins, CO (US)

(72) Inventors: Kenneth F. Reardon, Fort Collins, CO (US); Xingfeng Huang, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 26 days.

(21) Appl. No.: 17/240,613

(22) Filed: Apr. 26, 2021

Related U.S. Application Data

(60) Provisional application No. 63/043,878, filed on Jun. 25, 2020.

(51) Int. Cl.
  *C12P 7/22* (2006.01)
  *C12N 1/18* (2006.01)
  *C12P 7/06* (2006.01)
  *C12R 1/865* (2006.01)

(52) U.S. Cl.
  CPC .............. *C12P 7/22* (2013.01); *C12N 1/185* (2021.05); *C12P 7/06* (2013.01); *C12R 2001/865* (2021.05)

(58) Field of Classification Search
  None
  See application file for complete search history.

(56) References Cited

U.S. PATENT DOCUMENTS

| 4,350,765 | A | * | 9/1982 | Chibata | ............... C12M 25/14 426/11 |
| 8,394,622 | B2 | | 3/2013 | Forrester et al. | |
| 8,507,217 | B2 | | 8/2013 | Dmytruk et al. | |

FOREIGN PATENT DOCUMENTS

JP  2009131168 A  *  6/2009

OTHER PUBLICATIONS

JP2009131168. Jun. 18, 2009. Machine translation. (Year: 2009).*
Oliveira et al. Food Research International (2011), 44(7), 2391-2400 (Year: 2011).*
Argueso, J. L., Carazzolle, M. F., Mieczkowski, P. A., Duarte, F. M., Netto, O. V., Missawa, S. K., Galzerani, F., Costa, G. G., Vidal, R. O., Noronha, M. F., Dominska, M., Andrietta, M. G., Andrietta, S. R., Cunha, A. F., Gomes, L. H., Tavares, F. C., Alcarde, A. R., Dietrich, F. S., McCusker, J. H., Petes, T. D., . . . Pereira, G. A. (2009). Genome structure of a *Saccharomyces cerevisiae* strain widely used in bioethanol production. Genome research, 19(12), 2258-2270. https://doi.org/10.1101/gr.091777.109.

Adegboye, M.F., Ojuederie, O.B., Talia, P.M et al. Bioprospecting of microbial strains for biofuel production: metabolic engineering, applications, and challenges. Biotechnol Biofuels 14, 5 (2021). https://doi.org/10.1186/s13068-020-01853-2.
Avbelj, M., Zupan, J., Kranjc, L., & Raspor, P. (2015). Quorum-Sensing Kinetics in *Saccharomyces cerevisiae*: a Symphony of ARO Genes and Aromatic Alcohols. Journal of Agricultural and Food Chemistry, 63(38), 8544-8550. doi:10.1021/acs.jafc.5b03400.
Benisch F, Boles E. The bacterial Entner-Doudoroff pathway does not replace glycolysis in *Saccharomyces cerevisiae* due to the lack of activity of iron-sulfur cluster enzyme 6-phosphogluconate dehydratase. J Biotechnol. Feb. 10, 2014;171:45-55. doi: 10.1016/j.jbiotec.2013.11.025. Epub Dec. 11, 2013. PMID: 24333129.
Björkqvist, S., Ansell, R., Adler, L., & Liden, G. (1997). Physiological response to anaerobicity of glycerol-3-phosphate dehydrogenase mutants of *Saccharomyces cerevisiae*. Applied and environmental microbiology, 63(1), 128-132. https://doi.org/10.1128/aem.63.1.128-132.1997.
Brar, G. A., Yassour, M., Friedman, N., Regev, A., Ingolia, N. T., & Weissman, J. S. (2012). High-resolution view of the yeast meiotic program revealed by ribosome profiling. Science (New York, N.Y.), 335(6068), 552-557. https://doi.org/10.1126/science.1215110.
Bro C, Regenberg B, Forster J, Nielsen J. In silico aided metabolic engineering of *Saccharomyces cerevisiae* for improved bioethanol production. Metab Eng. Mar. 2006;8(2):102-11. doi: 10.1016/j.ymben.2005.09.007. Epub Nov. 10, 2005. PMID: 16289778.
Bušić, A., Mardetko, N., Kundas, S., Morzak, G., Belskaya, H., IvančićŠantek, M., Komes, D., Novak, S., & Šantek, B. (2018). Bioethanol Production from Renewable Raw Materials and Its Separation and Purification: a Review. Food technology and biotechnology, 56(3), 289-311. https://doi.org/10.17113/ftb.56.03.18.5546.
Chen, H., & Fink, G. R. (2006). Feedback control of morphogenesis in fungi by aromatic alcohols. Genes & development, 20(9), 1150-1161. https://doi.org/10.1101/gad.1411806.
Dinh CV, Chen X, Prather KLJ. Development of a Quorum-Sensing Based Circuit for Control of Coculture Population Composition in a Naringenin Production System. ACS Synthetic Biology. Mar. 2020;9(3):590-597. DOI: 10.1021/acssynbio.9b00451. PMID: 32040906.

(Continued)

*Primary Examiner* — Christian L Fronda
(74) *Attorney, Agent, or Firm* — Michael M. McGaw; McGaw Law, P.C.

(57) ABSTRACT

Methods and systems for the enhancement of bioproduct process yields. The present invention provides systems and methods for improvement of the carbon conversion efficiency by yeast of an organic substrate such as a fermentable sugar to a fermentation product such as ethanol. Exemplary yield-increasing/growth-inhibitory compounds include tyrosol (TyrOH), 2-phenylethanol (PheOH), and tryptophol (TrpOH). Immobilization of the yeast, such as in a porous bead or pellet, can further increase yield. Exemplary immobilization included immobilization in calcium alginate beads. The system and methods taught herein demonstrate that product yield such as ethanol yield can be improved by adding yeast yield-increasing/growth-inhibitory molecules to reduce cell growth of yeast species, such as *S. cerevisiae*, suggesting a strategy to improve the yield of ethanol and other yeast fermentation products by manipulating native biological control systems.

14 Claims, 10 Drawing Sheets

(56) References Cited

OTHER PUBLICATIONS

Gerashchenko, M. V., Lobanov, A. V., & Gladyshev, V. N. (2012). Genome-wide ribosome profiling reveals complex translational regulation in response to oxidative stress. Proceedings of the National Academy of Sciences of the United States of America, 109(43), 17394-17399. https://doi.org/10.1073/pnas.1120799109.

Gombert AK, van Maris AJ. Improving conversion yield of fermentable sugars into fuel ethanol in 1st generation yeast-based production processes. Curr Opin Biotechnol. Jun. 2015;33:81-6. doi: 10.1016/j.copbio.2014.12.012. Epub Jan. 7, 2015. PMID: 25576737.

González B, Vázquez J, Cullen PJ, Mas A, Beltran G, Torija MJ. Aromatic Amino Acid-Derived Compounds Induce Morphological Changes and Modulate the Cell Growth of Wine Yeast Species. Front Microbiol. Apr. 11, 2018;9:670. doi: 10.3389/fmicb.2018.00670. PMID: 29696002; PMCID: PMC5904269.

Guadalupe-Medina, V., Wisselink, H. W., Luttik, M. A., de Hulster, E., Daran, J. M., Pronk, J. T., & van Maris, A. J. (2013). Carbon dioxide fixation by Calvin-Cycle enzymes improves ethanol yield in yeast. Biotechnology for biofuels, 6 (1), 125. https://doi.org/10.1186/1754-6834-6-125.

Hahn-Hägerdal B, Karhumaa K, Fonseca C, Spencer-Martins I, Gorwa-Grauslund MF. Towards industrial pentose-fermenting yeast strains. Appl Microbiol Biotechnol. Apr. 2007;74(5):937-53. doi: 10.1007/s00253-006-0827-2. Epub Feb. 9, 2007. PMID: 17294186.

Hazelwood, L. A., Daran, J. M., van Maris, A. J., Pronk, J. T., & Dickinson, J. R. (2008). The Ehrlich pathway for fusel alcohol production: a century of research on *Saccharomyces cerevisiae* metabolism. Applied and environmental microbiology, 74(8), 2259-2266. https://doi.org/10.1128/AEM.02625-07.

Hornby, J. M., Jensen, E. C., Lisec, A. D., Tasto, J. J., Jahnke, B., Shoemaker, R., Dussault, P., & Nickerson, K. W. (2001). Quorum sensing in the dimorphic fungus Candida albicans is mediated by farnesol. Applied and environmental microbiology, 67(7), 2982-2992. https://doi.org/10.1128/AEM.67.7.2982-2992.2001.

Kurylenko O, Semkiv M, Ruchala J, Hryniv O, Kshanovska B, Abbas C, Dmytruk K, Sibirny A. New approaches for improving the production of the 1st and 2nd generation ethanol by yeast. Acta Biochim Pol. 2016;63(1):31-38. doi: 10.18388/abp.2015_1156. Epub Nov. 30, 2015. PMID: 26619255.

Guadalupe Medina, V., Almering, M. J., van Maris, A. J., & Pronk, J. T. (2010). Elimination of glycerol production in anaerobic cultures of a *Saccharomyces cerevisiae* strain engineered to use acetic acid as an electron acceptor. Applied and environmental microbiology, 76(1), 190-195. https://doi.org/10.1128/AEM.01772-09.

Miller MB, Bassler BL. Quorum sensing in bacteria. Annu Rev Microbiol. 2001;55:165-99. doi: 10.1146/annurev.micro.55.1.165. PMID: 11544353.

Moehle, C. M., & Hinnebusch, A. G. (1991). Association of RAP1 binding sites with stringent control of ribosomal protein gene transcription in *Saccharomyces cerevisiae*. Molecular and Cellular Biology, 11(5), 2723. doi:10.1128/MCB.11.5.2723.

Naghshbandi, M. P., Tabatabaei, M., Aghbashlo, M., Gupta, V. K., Sulaiman, A., Karimi, K., . . . Maleki, M. (2019). Progress toward improving ethanol production through decreased glycerol generation in *Saccharomyces cerevisiae* by metabolic and genetic engineering approaches. Renewable and Sustainable Energy Reviews, 115, 109353. doi:https://doi.org/10.1016/j.rser.2019.109353.

Nissen TL, Kielland-Brandt MC, Nielsen J, Villadsen J. Optimization of ethanol production in *Saccharomyces cerevisiae* by metabolic engineering of the ammonium assimilation. Metab Eng. Jan. 2000;2(1):69-77. doi: 10.1006/mben.1999.0140. PMID: 10935936.

Papapetridis I, Goudriaan M, Vázquez Vitali M, de Keijzer NA, van den Broek M, van Maris AJA, Pronk JT. Optimizing anaerobic growth rate and fermentation kinetics in *Saccharomyces cerevisiae* strains expressing Calvin-cycle enzymes for improved ethanol yield. Biotechnol Biofuels. Jan. 25, 2018;11:17. doi: 10.1186/s13068-017-1001-z. PMID: 29416562; PMCID: PMC5784725.

Papapetridis, I., van Dijk, M., van Maris, A.J.A et al. Metabolic engineering strategies for optimizing acetate reduction, ethanol yield and osmotolerance in *Saccharomyces cerevisiae*. Biotechnol Biofuels 10, 107 (2017). https://doi.org/10.1186/s13068-017-0791-3.

Robak K, Balcerek M. Current state-of-the-art in ethanol production from lignocellulosic feedstocks. Microbiol Res. Nov. 2020;240:126534. doi: 10.1016/j.micres.2020.126534. Epub Jun. 27, 2020. PMID: 32683278.

Semkiv, M.V., Dmytruk, K.V., Abbas, C.A et al. Increased ethanol accumulation from glucose via reduction of ATP level in a recombinant strain of *Saccharomyces cerevisiae* overexpressing alkaline phosphatase. BMC Biotechnol 14, 42 (2014). https://doi.org/10.1186/1472-6750-14-42.

Semkiv, M. V., Dmytruk, K. V., Abbas, C. A., & Sibirny, A. A. (2016). Activation of futile cycles as an approach to increase ethanol yield during glucose fermentation in *Saccharomyces cerevisiae*. Bioengineered, 7(2), 106-111. https://doi.org/10.1080/21655979.2016.1148223.

Vallejo, B., Picazo, C., Orozco, H. et al. Herbicide glufosinate inhibits yeast growth and extends longevity during wine fermentation. Sci Rep 7, 12414 (2017). https://doi.org/10.1038/s41598-017-12794-6.

Walker GM, Stewart GG. *Saccharomyces cerevisiae* in the Production of Fermented Beverages. Beverages. 2016; 2 (4):30. https://doi.org/10.3390/beverages2040030.

Westman JO, Franzén CJ. Current progress in high cell density yeast bioprocesses for bioethanol production. Biotechnol J. Aug. 2015;10(8):1185-95. doi: 10.1002/biot.201400581. Epub Jul. 24, 2015. PMID: 26211654.

Zhang L, Tang Y, Guo ZP, Ding ZY, Shi GY. Improving the ethanol yield by reducing glycerol formation using cofactor regulation in *Saccharomyces cerevisiae*. Biotechnol Lett. Jul. 2011;33(7):1375-80. doi: 10.1007/s10529-011-0588-6. Epub Mar. 13, 2011. PMID: 21400237.

\* cited by examiner

A

B
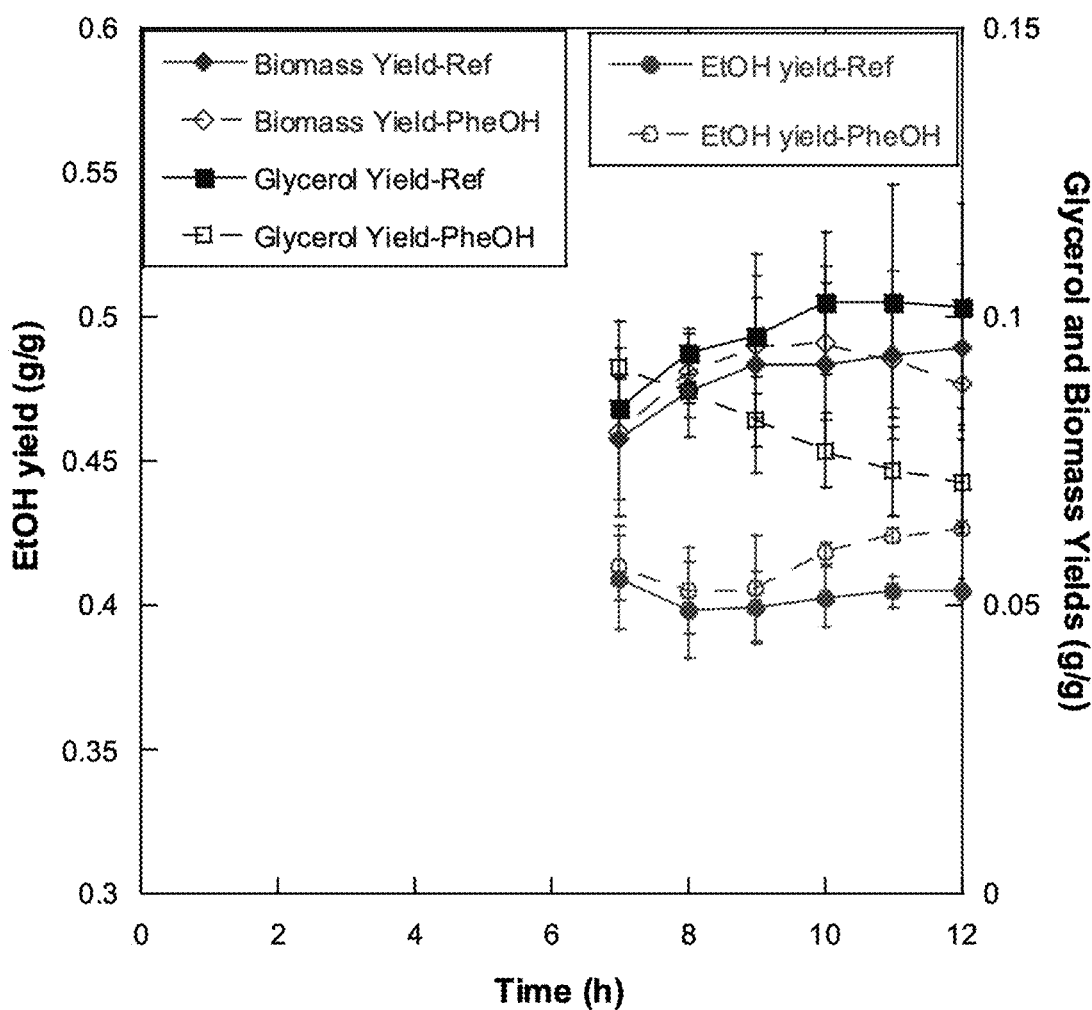
*FIG. 2 - continued*

A

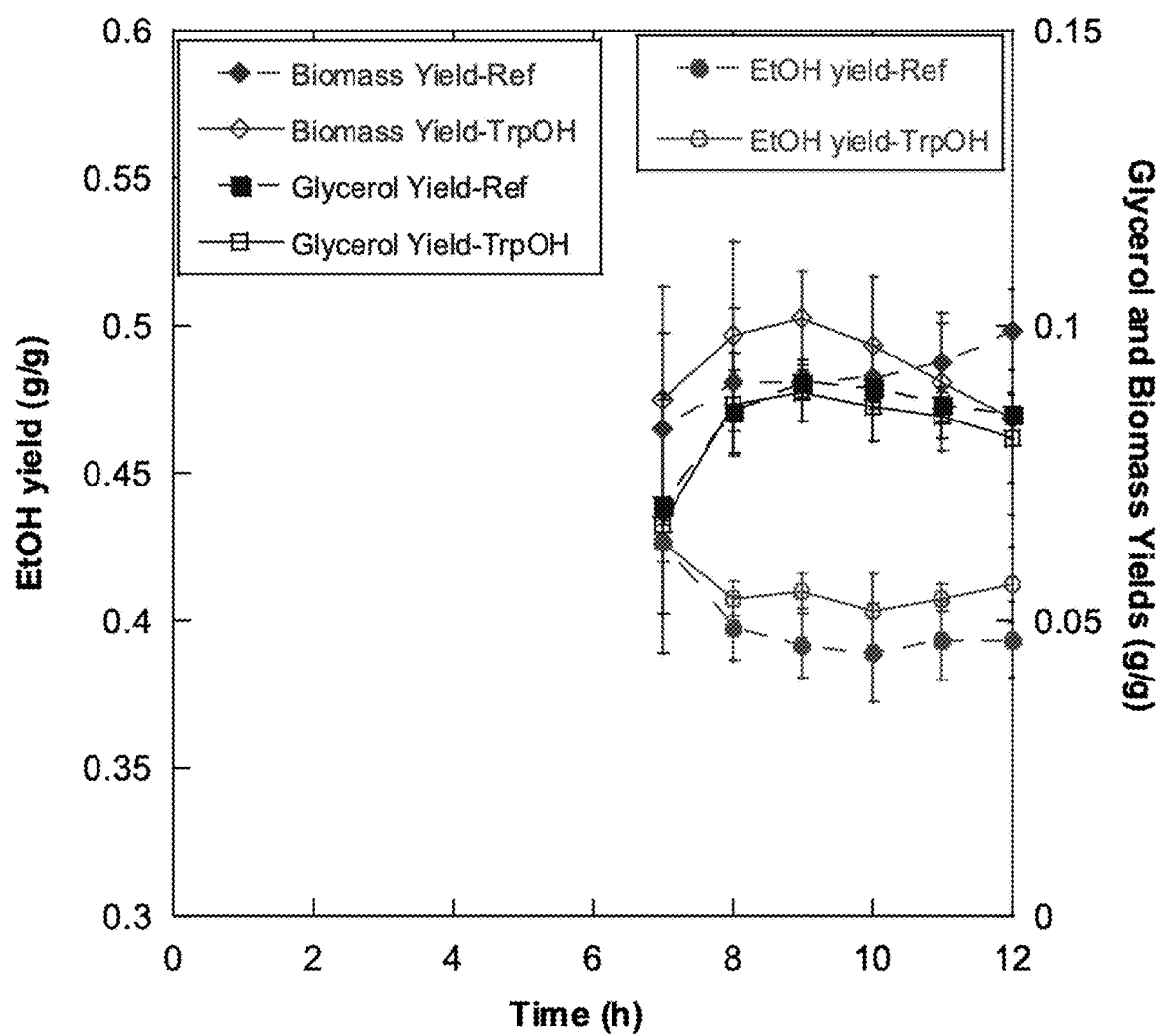
FIG. 3 - continued

METHODS FOR THE CONVERSION OF FERMENTABLE SUGARS TO ETHANOL

CROSS-REFERENCE TO RELATED APPLICATIONS

This application claims the benefit of U.S. Provisional Application No. 63/043,878, filed Jun. 25, 2020.

STATEMENT OF GOVERNMENT INTEREST

This invention was made with government support under grant number DE-AC36-08GO28308 awarded by the Department of Energy. The government has certain rights in the invention.

FIELD OF INVENTION

This invention relates to methods and systems for the reduction of carbon flux to biomass. More specifically, the invention relates to the application of certain growth inhibitor treatments to increase product yields of bioprocesses.

BACKGROUND OF THE INVENTION

Non-renewable fossil fuels, coal, oil and natural gas, are currently the world's primary energy sources and are the starting points for the production of most chemicals. However, the continuous increase of energy use, depletion of fossil fuel reserves, and climate change issues have driven substantial research efforts in renewable and sustainable fuel and chemical alternatives. Biofuels and other chemicals produced from biomass feedstocks are an attractive alternative to fossil fuels for future energy security and have been proven to have much lower greenhouse gas footprints [Adegboye, M. F., Ojuederie, O. B., Talia, P. M., & Babalola, O. O. (2021). Bioprospecting of microbial strains for biofuel production: metabolic engineering, applications, and challenges. *Biotechnology for Biofuels*, 14(1), 5. doi:10.1186/s13068-020-01853-2]. Bioprocesses that convert biomass-derived substrates to fuels and other valuable products are the backbone of the bioeconomy and have the ability to increase the sustainability of chemical manufacturing. A key factor in the economic and environmental sustainability of bioprocesses is the yield of the desired product [Gombert, A. K., & van Maris, A. J. A. (2015). Improving conversion yield of fermentable sugars into fuel ethanol in 1st generation yeast-based production processes. *Current Opinion in Biotechnology*, 33, 81-86. doi:https://doi.org/10.1016/j.copbio.2014.12.012]

Ethanol is the bio-based product produced the largest quantity. Global bioethanol production grew from less than one billion liters in 1975 to more than 100 billion liters in 2016 and is expected to increase to 134.5 billion liters by 2024 [Bušić, A., et al., (2018). Bioethanol Production from Renewable Raw Materials and Its Separation and Purification: A Review. *Food technology and Biotechnology*, 56(3), 289-311. doi:10.17113/ftb 0.56.03.18.5546]. The yeast *Saccharomyces cerevisiae* is the most employed microorganism for industrial ethanol production because it is generally recognized as safe (GRAS) and is superior to other yeasts or bacteria in various physiological characteristics including tolerance to a wide range of physiological stresses such as low pH, high ethanol concentration, and high osmotic stress [Hahn-Hägerdal, B., Karhumaa, K., Fonseca, C., Spencer-Martins, I., & Gorwa-Grauslund, M. F. (2007). Towards industrial pentose-fermenting yeast strains. *Applied Microbiology and Biotechnology*, 74(5), 937-953. doi:10.1007/s00253-006-0827-2]. Under anaerobic conditions, *S. cerevisiae* converts sugars, including glucose, maltose, fructose, mannose, galactose, sucrose, and maltotriose, into ethanol [Walker, G. M., & Stewart, G. G. (2016). *Saccharomyces cerevisiae* in the Production of Fermented Beverages. *Beverages*, 2(4), 30.]. The theoretical maximum conversion to ethanol from glucose by *S. cerevisiae* is 51% (w/w). In real fermentations, some glucose carbon is used for cell growth and synthesis of other metabolites such as glycerol, and thus only ~90% of this theoretical conversion can be obtained in industrial fermentation (Bušićet al., 2018). In second-generation bioethanol production from lignocellulosic biomass, reduced bioethanol yield and productivity are often reported because of the presence of toxic compounds in hydrolysates that negatively affect the activity of metabolic enzymes and yeast cell growth during fermentation [Robak, K., & Balcerek, M. (2020). Current state-of-the-art in ethanol production from lignocellulosic feedstocks. *Microbiological Research*, 240, 126534.].

The economic and environmental sustainability of all bioprocesses (e.g., ethanol, lactic acid, riboflavin) depends on the efficiency (yield) with which the carbon in the substrate is converted to the desired product due to the resources required to produce sugars and other substrates required for microbial cultivations. One major factor in the conversion efficiency is the production of cellular biomass (growth) by the microorganisms. (See e.g. FIG. 1) Resources used for the production of cellular biomass (growth) by the microorganisms are unavailable for the production of alternative bioproducts. The present invention provides systems and methods to alter the balance of the utilization of key carbon inputs by limiting the use of resources for the production of cellular biomass in favor of alternative fermentation products as will become apparent in the following disclosure.

SUMMARY OF THE INVENTION

The present invention provides systems and methods for improvement of the carbon conversion efficiency of an organic substrate such as a sugar. The addition of growth-inhibitory compounds results in increased yield of a desired product such as ethanol. In combination with cell immobilization and certain bioreactor configurations, the present invention can lead to increased productivity and substrate utilization. It is contemplated that the present invention is applicable to conversion of any fermentable substrates (sugars or other) from any source, whether that is sugar cane, sugar beets, plant biomass hydrolysate, algal hydrolysate, or anything other substance that can be utilized in a fermentation process.

In a first aspect the present invention provides a method for the increased conversion of an organic substrate to a fermentation product. The method includes the steps of providing a population of yeast cells, providing a yield-increasing compound (e.g. an aromatic alcohol) such as tyrosol (TyrOH) or an analog or derivative thereof, 2-phenylethanol (PheOH) or an analog or derivative thereof, tryptophol (TrpOH) or an analog or derivative thereof, and combinations of the aforementioned yield-increasing compounds, fermenting the organic substrate with the yeast cells in the presence of the yield-increasing compound, and collecting the resultant fermentation product from the fermentation. It is contemplated that derivatives of tyrosol, 2-phenylethanol, or tryptophol, such as through the addition of alkyl, hydroxyl, or carboxyl groups to the aforementioned compounds, may be created that may exhibit activity matching or exceeding tyrosol, 2-phenylethanol or tryptophol. One of ordinary skill in the art can create such compounds and screen them for the desired activity (e.g. yield-increasing in yeast fermentations).

In certain embodiments the yeast cells are immobilized prior to the fermentation process. In further embodiments the yeast cells are a yeast cell from the genus *Saccharomyces*. In an advantageous embodiment the yeast cell is *S. cerevisiae, S. paradoxus, S. kudriavzezii,* or *S. mikatae*. In a particularly advantageous embodiment the yeast cell is *Saccharomyces cerevisiae*.

It is contemplated that the methods of the invention, including the methods of the first aspect, will find application in producing products including organic acids (e.g. lactic acid, pyruvic acid, formic acid, acetic acid, succinic acid, malic acid, 3-hydroxypropionic acid, fumaric acid, muconic acid, and citric acid), alcohols (e.g. ethanol, n-butanol, 1-butanol, 2-methyl-1-butanol, 1-propanol, 1,2-propanediol, and 3-methyl-1-butanol), fatty acids (e.g. linolenic acid, stearidonic acid, arachinoic acid, eicosapentaenoic acid and hexadecadienoic acid), isoprenoids (e.g. bisabolene, patchoulol, cubebol, farnesol, sesquiterpenes, taxadiene, alpha-santalene, sterols, carotenoids, taxol, and casbene), non-natural stilbenes (e.g. lycopene) and non-natural dihydrochalcones (e.g. L-ascorbic acid, beta-amyrin, and ribotol), cinnamoyl anthranilates, beta-carotene, polyhydroxylalkanoates, reservatol, se-methyl selenocysteine, glycerol, and artemisinic acid, among other commercially important fermentation products. In an advantageous embodiment the fermentation product is ethanol, lactic acid, riboflavin, ethyl acetate, arabinitol, glycerol, xylitol, or resveratrol. In a particularly advantageous embodiment the fermentation product is ethanol.

The tyrosol, 2-phenylethanol or tryptophol (or an analogs or derivatives thereof), can be at a concentration of about 0.05% to about 0.30%, more than 0.10% to about 0.30%, or about 0.12% to about 0.25%. In further embodiments the tyrosol, 2-phenylethanol or tryptophol (or an analogs or derivatives thereof), can be at a concentration of in excess of 0.10%, in excess of 0.12%, in excess of 0.15%, or in excess of in excess of 0.20%.

In a second aspect the present invention provides a method for the increased conversion of a fermentable sugar to a fermentation product. The method includes the steps of comprising the steps of providing a population of yeast cells, contacting the yeast cells with a yield-increasing compound that allows for the production of the fermentation product, fermenting the fermentable sugar with the yeast cells in the presence of the yield-increasing compound, and collecting the resultant product from the fermentation.

In certain embodiments, the method of the second aspect includes immobilizing the yeast cells prior to the fermentation step. The yeast cells can be immobilized in a porous matrix or porous bead such as in calcium alginate.

In an advantageous embodiment the fermentation product of the method according to the second aspect is ethanol, lactic acid, riboflavin, ethyl acetate, arabinitol, glycerol, xylitol, or resveratrol. In further advantageous embodiments the yield-increasing compound is an aromatic alcohol. Particularly advantageous aromatic alcohols include tyrosol, 2-phenylethanol, tryptophol, or analogs or derivatives of tyrosol, 2-phenylethanol, tryptophol. The concentration of tyrosol, 2-phenylethanol, tryptophol can be greater than 0.05% to about 0.3%, greater than 0.10% to about 0.3%, or about 0.120% to about 0.250%. The yeast cell can be *S. cerevisiae, S. paradoxus, S. kudriavzezii, S. mikatae, Pichia stipites, Wickerhamomyces anomalous, Pichia fermentans, Saccharomyces pastorianus, Pichia pastoris, Schizosaccharomyces pombe,* and *Kluyveromyces fragilis*.

In a third aspect the present invention provides a method of enhancing a fermentation yield. The method can include the steps of comprising the steps of providing cells of a yeast strain, fermenting a fermentable substrate with the provided yeast cells in the presence of tyrosol or an analog or derivative thereof, 2-phenylethanol or an analog or derivative thereof, tryptophol or an analog or derivative thereof, or a combination thereof under conditions effective to produce a desired bioproduct, and collecting the resultant bioproduct from the fermentation. The yeast strain can be a yeast strain selected from the group species consisting of *S. cerevisiae, S. paradoxus, S. kudriavzezii, S. mikatae, Pichia stipites, Wickerhamomyces anomalous, Pichia fermentans, Saccharomyces pastorianus, Pichia pastoris* and *Kluyveromyces fragilis*. In an advantageous embodiment the yeast strain is a *Saccharomyces* strain. In further advantageous embodiments the yeast strain is a strain that has been genetically engineered to reduce production of significant bioprocess byproducts such as glycerol.

In a fourth aspect the present invention provides a method for the increased conversion of a fermentable sugar to ethanol. The method according to the fourth aspect can include the steps of providing a *S. cerevisiae* strain, fermenting the sugar with the immobilized *S. cerevisiae* strain cells in the presence of tyrosol or an analog or derivative thereof, 2-phenylethanol or an analog or derivative thereof, tryptophol or an analog or derivative thereof, or a combination of the aforementioned compounds, and collecting the resultant ethanol from the fermentation. The tyrosol, 2-phenylethanol or tryptophol (or an analogs or derivatives thereof), can be at a concentration of about 0.05% to about 0.30%, more than 0.10% to about 0.30%, about 0.20% to about 0.50%, or about 0.12% to about 0.25%. In further embodiments the tyrosol, 2-phenylethanol or tryptophol (or an analogs or derivatives thereof), can be at a concentration of in excess of 0.10%, in excess of 0.12%, in excess of 0.15%, or in excess of in excess of 0.20%. In certain embodiments, the method of the fourth aspect includes immobilizing the yeast cells prior to the fermentation step. The yeast cells can be immobilized in a porous matrix or porous bead such as in calcium alginate.

BRIEF DESCRIPTION OF THE DRAWINGS

For a fuller understanding of the invention, reference should be made to the following detailed description, taken in connection with the accompanying drawings, in which:

FIG. 3 is a pair of graphs (A and B) showing the results of tryptophol (TrpOH) addition in bioreactors containing *S.* cerevisiae JAY 270. TrpOH (final concentration 0.12%) was added to the treatment bioreactor and the same amount of DMSO was added to the reference bioreactor at 7 hours. This experiment was repeated in triplicate. (A): The change of glucose, ethanol, glycerol, and biomass (as OD600) concentrations during fermentation. (B): The change of ethanol, glycerol, and biomass yields after TrpOH was added to the treatment bioreactor at 7 hours. The error bars are the standard deviations from 3 biological replicates.

Figure 4:
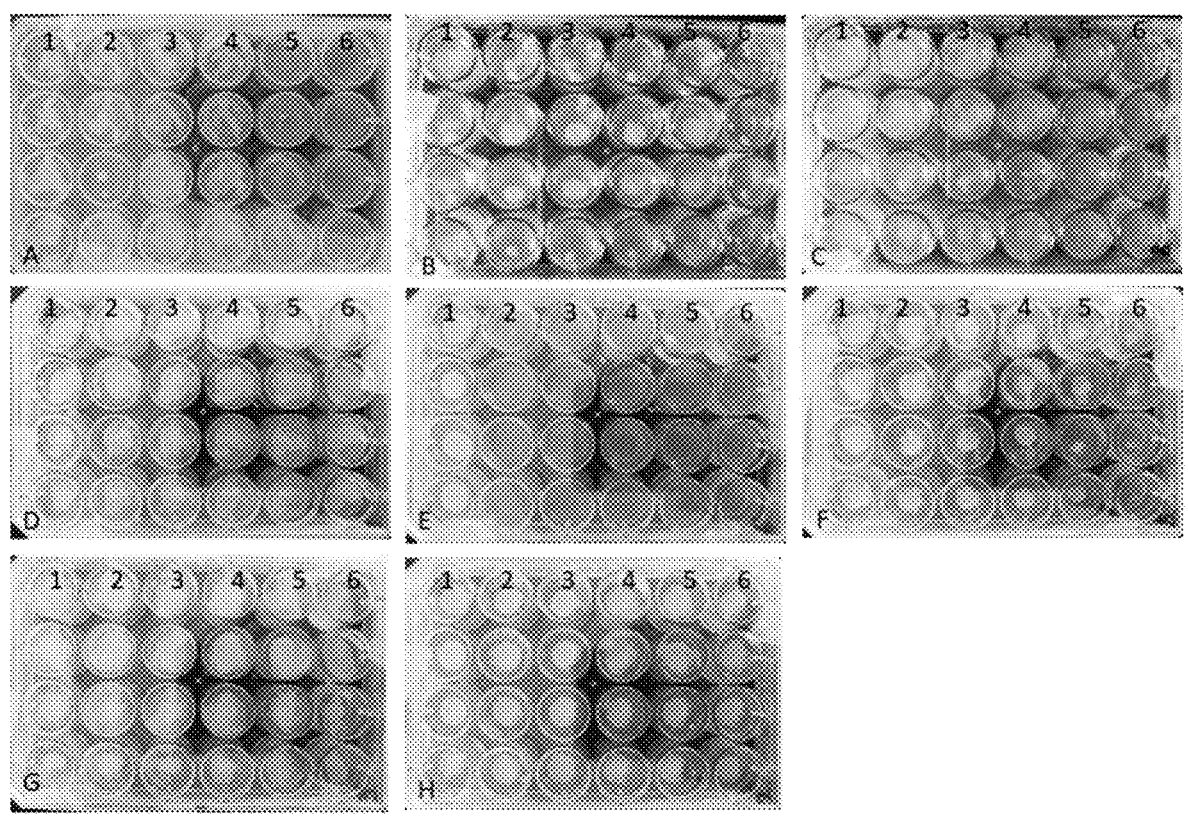

FIG. 4 is an image showing eight 24-well plates. Eight chemicals with potential as yeast growth inhibitors were tested on S. cerevisiae JAY 270 in 24-well plates. As shown in the figure, these tested compounds had different effects on the cell growth of S. cerevisiae JAY 270 in the plate assay. TyrOH: tyrosol, PheOH: 2-phenylethanol, TrpOH: tryptophol. PheOH, TrpOH, TyrOH, boric acid, and cycloheximide inhibited growth, although at different concentrations. (A): PheOH. 1: reference; 2: 0.03%; 3: 0.05%; 4: 0.1%; 5: 0.2%; 6: 0.4%. (B): TyrOH. 1: reference; 2: DMSO 0.2%; 3: 0.03%; 4: 0.05%; 5: 0.1%; 6: 0.2%. (C): TrpOH. 1: reference; 2: DMSO 0.2%; 3: 0.03%; 4: 0.05%; 5: 0.1%; 6: 0.2%. (D): Farnesol. 1: reference; 2: 0.01%; 3: 0.03%; 4: 0.05%; 5: 0.1%; 6: 0.2%. (E): Cycloheximide. 1: reference; 2: 0.01%; 3: 0.03%; 4: 0.05%; 5: 0.1%; 6: 0.2%. (F): Boric acid. 1: reference; 2: 0.01%; 3: 0.03%; 4: 0.05%; 5: 0.1%; 6: 0.2%. (G): Glufosinate ammonium. 1: reference; 2: 0.01%; 3: 0.03%; 4: 0.05%; 5: 0.1%; 6: 0.2%. (H): 3-amino-1,2,4triazole. 1: reference; 2: 0.01%; 3: 0.03%; 4: 0.05%; 5: 0.1%; 6: 0.2%.

Figure 5:
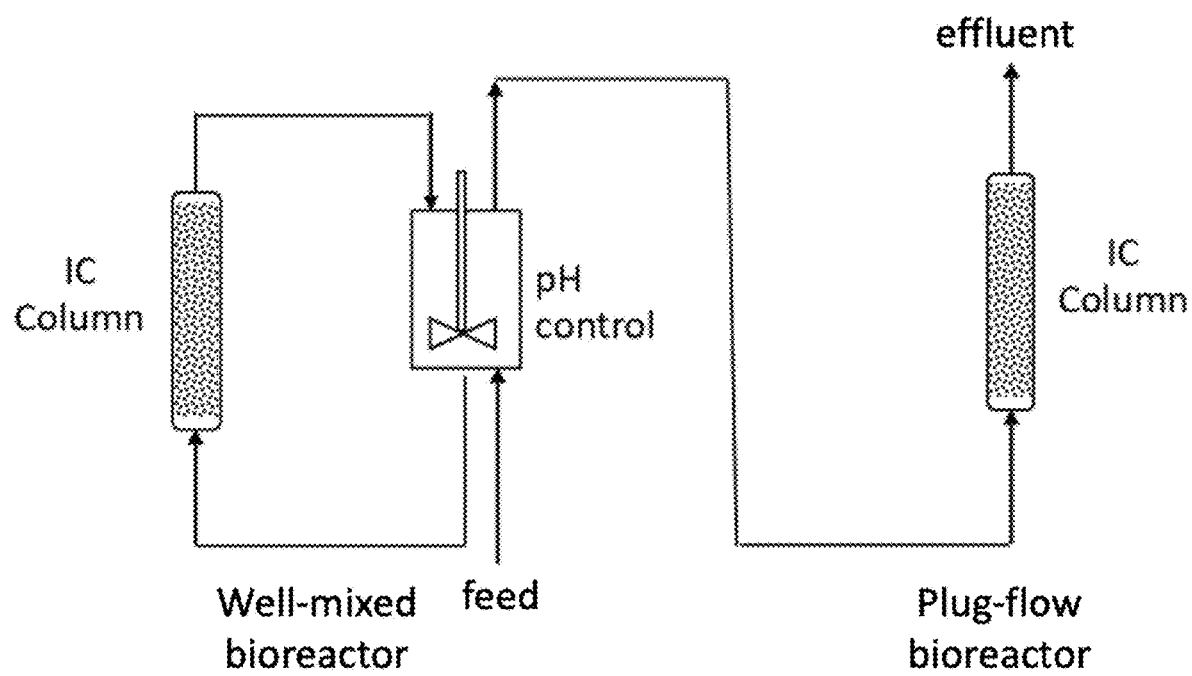

FIG. 5 is a schematic diagram of a two-part, immobilized-cell bioreactor system according to aspects of the invention.

Figure 6:
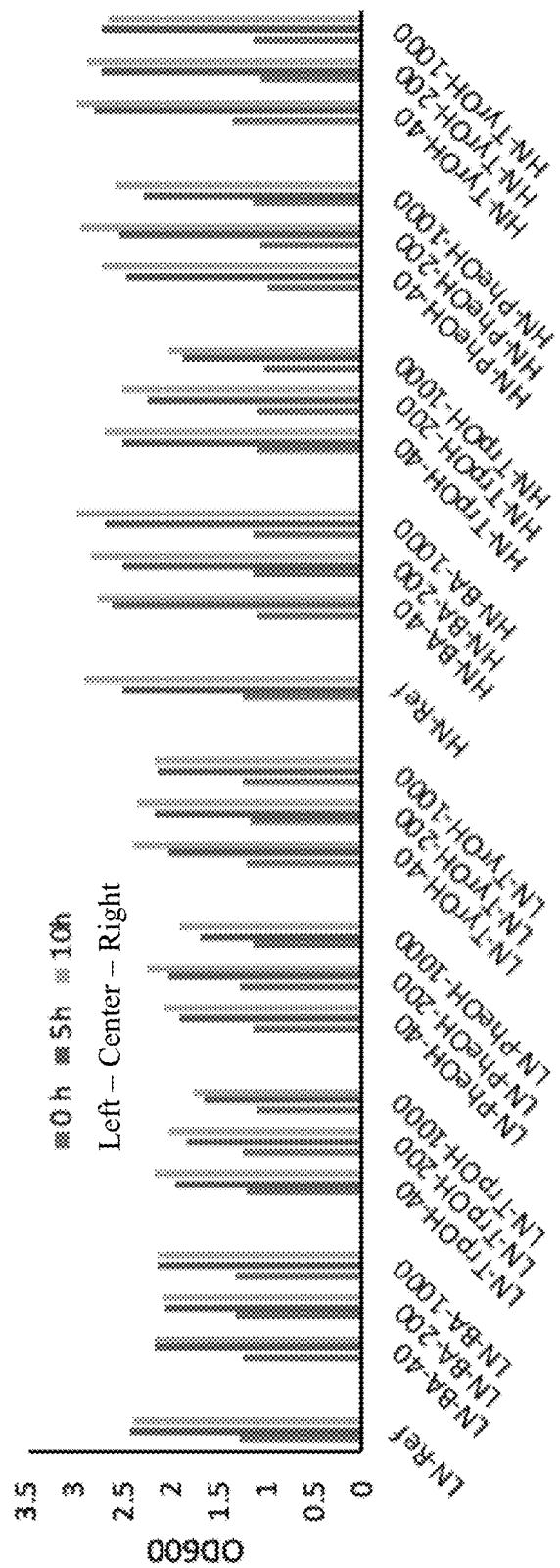

FIG. 6 is a graph showing the effects of four compounds on S. cerevisiae JAY 270 growth in YNB medium. TyrOH: tyrosol, PheOH: 2-phenylethanol, TrpOH: tryptophol, BA: boric acid. LN: low (1 mM) nitrogen medium, HN: high (10 mM) nitrogen medium. Concentrations tested were 40 mg/L (40), 200 mg/L (200), and 1000 mg/L (1000).

Figure 7:
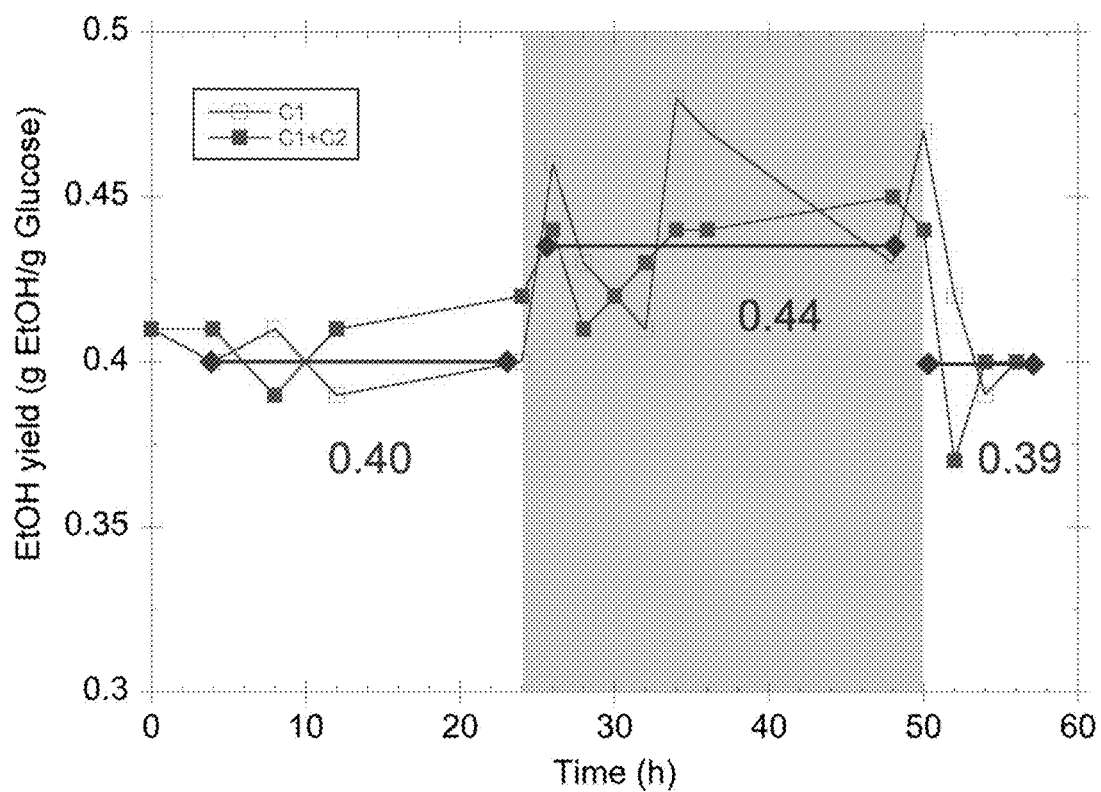
Figure 7:
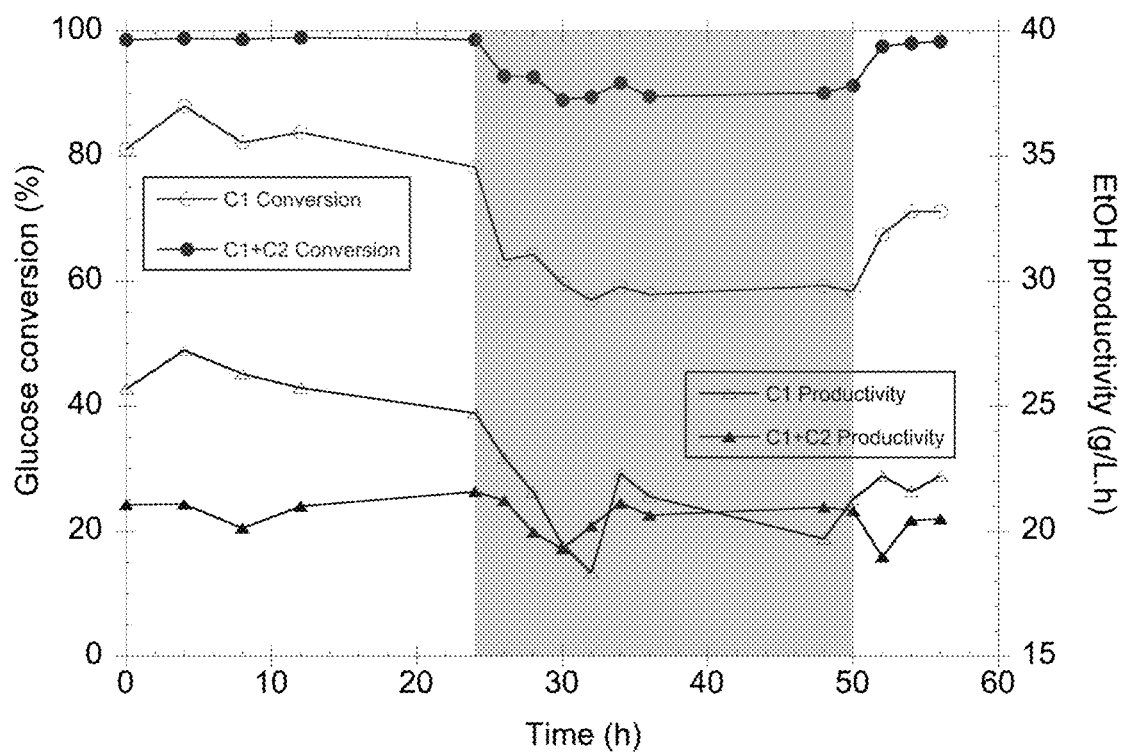

FIG. 7 is a pair of graphs showing the effects of PheOH addition during continuous-flow, two-stage immobilized cell bioreactor experiment with S. cerevisiae JAY 270. During the first 24 hours, the feed to the bioreactor system contained only yeast extract-peptone-dextrose (YPD) medium with 20 g/L glucose. During the next 26-hour period, indicated with gray shading, the system was fed YPD+0.2% PheOH. Finally, the bioreactor was fed YPD medium (no PheOH) for 6 hours. Top: Ethanol yield; values indicated are the mean for the period. Bottom: glucose conversion (upper two plots) and ethanol productivity (lower two plots). C1 indicates the first bioreactor stage and C1+C2 indicates the entire system.

Figure 8:
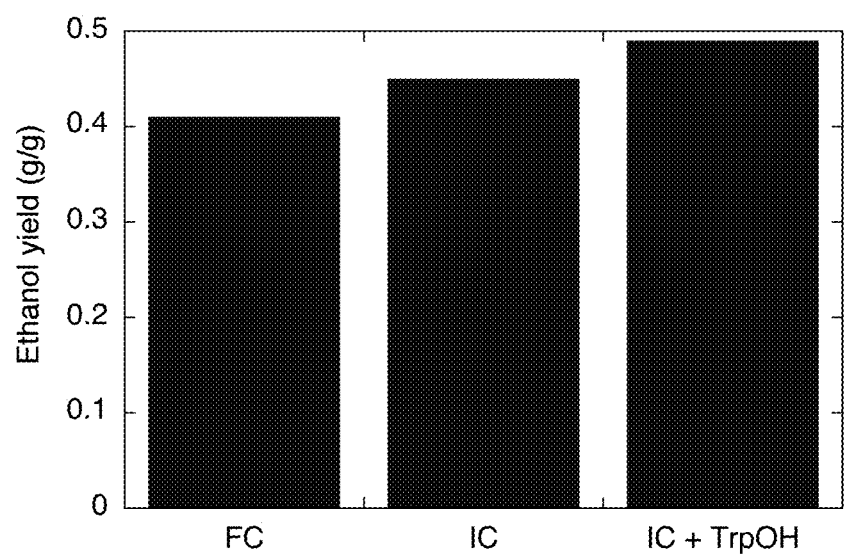

FIG. 8 is a graph showing increases in ethanol yield from S. cerevisiae JAY270 grown in batch cultivation on D. armatus hydrolysate. FC: free cells, IC: immobilized cells. TrpOH: tryptophol.

DETAILED DESCRIPTION OF THE PREFERRED EMBODIMENT

Part I: Demonstration of Effects of Yield-Increasing Molecules

Figure 1:
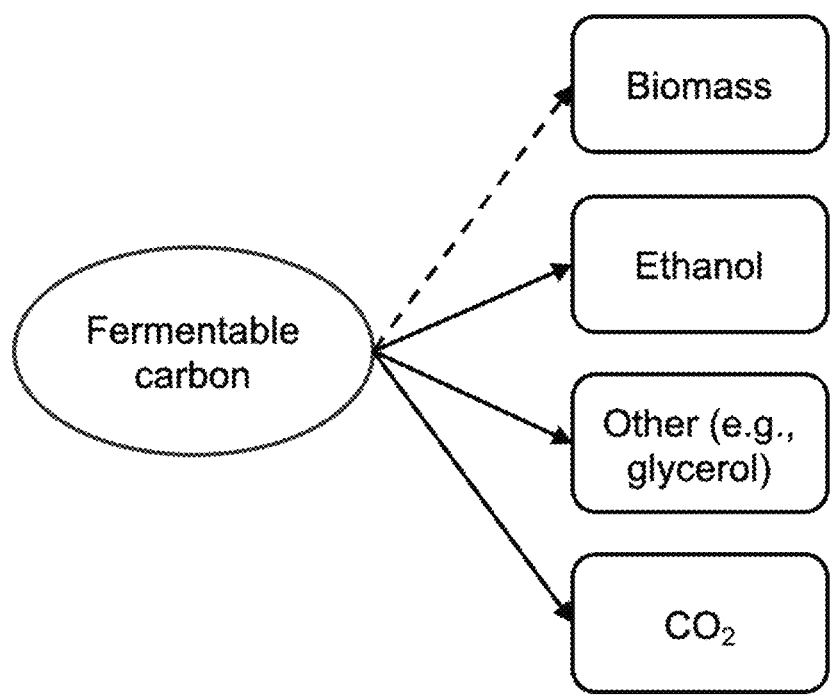
FIG. 1 is a diagram showing the overall distribution of substrate carbon to ethanol, biomass, and other products in ethanolic yeast fermentations. The present invention provides systems and methods for the reduction of carbon flux to biomass (see e.g. the dashed line in the figure).

One of the top priorities in bioprocessing, especially for bio-based products, is increased yield of the desired product from the substrate(s). One strategy to achieve this goal is to redirect substrate carbon from biomass synthesis to formation of the desired product (FIG. 1). The present invention provides chemicals and methods that inhibit the growth of yeast such as Saccharomyces cerevisiae while allowing bioproduct production (e.g., ethanol) with higher yields. A set of eight growth inhibition chemicals were screened for their ability to reduce cell growth using S. cerevisiae JAY 270 as an exemplary yeast in 24-well plates. Based on the results of this screening test, boric acid, cycloheximide, 2-phenylethanol, tryptophol, and tyrosol were selected for further evaluation. In the presence of 2-phenylethanol, tryptophol, and tyrosol in serum-bottle tests, S. cerevisiae cell growth was reduced while ethanol yield was increased. These three yield-increasing molecules were also tested with seven other yeast strains and the ethanol yield was found to increase up to 15%. The performance of 2-phenylethanol and tryptophol was also tested in 1-L bioreactor fermentations. It was found that the addition of 2-phenylethanol at 0.2% decreased the cell concentration by 22% and decreased the glycerol concentration by 21%, while the ethanol yield was 6% higher in the PheOH treatment than the control. The addition of tryptophol at 0.12% resulted in 22% lower cell concentration, 17% lower glycerol concentration, and 10% higher ethanol yield than in the control. The effects on cell growth and product yields including cellular biomass yield, glycerol yield, and ethanol yield of S. cerevisiae JAY 270 were determined. These findings demonstrate that the ethanol yield can be improved by adding certain yield-increasing molecules to reduce cell growth of S. cerevisiae, suggesting a strategy to improve the yield of ethanol and other yeast fermentation products by manipulating native biological control systems, such as quorum sensing.

Example 1: Screening of Potential Yeast Growth Inhibition Compounds

Yeast strain: S. cerevisiae JAY 270 was provided by Dr. Juan Lucas Argueso at Colorado State University. The strain was maintained as frozen stocks at −80° C. Fresh cultures on yeast extract-peptone-dextrose agar (YPDA: 10 g/L yeast extract, 20 g/L peptone, 20 g/L glucose, 15 g/L agar) plates were prepared and kept at 4° C. before use. S. cerevisiae JAY 270, a PE-2 derived diploid, is a widely used in bioethanol production [Argueso, J. L., et al., (2009). Genome structure of a Saccharomyces cerevisiae strain widely used in bioethanol production. Genome research, 19(12), 2258-2270. doi:10.1101/gr.091777.109].

Chemicals: All chemicals were of analytical grade. Tyrosol (TyrOH), 2-phenylethanol (PheOH), tryptophol (TrpOH), 3-amino-1,2,4-triazole (3-AT), and farnesol were from Alfa Aesar (Ward Hill, Massachusetts, United States). Boric acid, glufosinate ammonium (GA), and cycloheximide were from Sigma-Aldrich (St. Louis, Missouri, United States).

Procedure: An inoculum culture of S. cerevisiae JAY 270 was grown in 100 mL of yeast extract-peptone-dextrose (YPD) medium (10 g/L yeast extract, 20 g/L peptone, 20 g/L glucose) in 200-mL serum bottles overnight in a shaker at 30° C. and 200 rpm. The cells were collected by centrifuging 10 min at 4000×g and 4° C. To wash off the medium residue, the cell pellet was resuspended in 30 mL of sterile 0.8% (w/v) NaCl solution and centrifuged at 4000×g for 10 min. The cell pellet was washed twice. Finally, the cell pellet was resuspended and diluted in 0.8% (w/v) NaCl to achieve cell concentrations of OD600=0.02 and 0.2.

The extent of growth inhibition of eight chemicals was screened in 24-well plates containing YPD agar (YPDA) medium (YPD with 15 g/L agar) and the potential growth inhibitor chemicals. The eight compounds were added in YPDA separately at 0.03%, 0.05%, 0.1%, and 0.2% (w/v). The standard control treatment contained only YPDA medium without addition of these compounds. Since the TrpOH and TyrOH stock solutions were dissolved in DMSO, the controls for those tests were YPDA with the same concentration of DMSO. A 3-mL aliquot of YPDA medium with or without the test compounds were loaded in each well of the 24-well plate.

Ten μL of the prepared *S. cerevisiae* JAY 270 cell suspension at OD600=0.02 or 0.2 was loaded onto the YPDA medium in each well of the 24-well plates. Then the plates were sealed with Parafilm and incubated at 30° C. for 24 h. There were four biological replicates for each treatment.

Yeast cell growth was evaluated by visual observation of the colony size in the well and scored as 0, +, ++, and +++. The score "0" indicates no cell growth in the well, while "+++" means the treatment had a colony size similar to the control.

A second set of tests was performed in a defined liquid medium, Yeast Nitrogen Base with Glucose (YNB), containing $(NH_4)_2SO_4$ at either low (1 mM) or high (10 mM) nitrogen content. TyrOH, PheOH, and TrpOH and boric acid were tested at 40, 200, and 1000 mg/L. All serum bottles were incubated in a shaker at 30° C. and 150 RPM. Each treatment was performed in biological duplicate. Samples were collected at 0, 5, and 10 hours.

Results: As shown in Table 1 and FIG. 4, the tested compounds had different effects on the cell growth of *S. cerevisiae* JAY 270 in the plate assay. PheOH, TrpOH, TyrOH, boric acid, and cycloheximide inhibited growth, although at different concentrations. Cycloheximide inhibited all cell growth at all tested concentrations, while PheOH, TyrOH, and boric acid at 0.1% and higher concentrations exhibited significant cell growth inhibition. TrpOH had a stronger effect on cell growth than PheOH and TyrOH as it reduced cell growth at lower concentration (0.05% w/v, or 3.1 mM) while PheOH and TyrOH had similar effects at 0.1% (8.2 mM PheOH and 7.2 mM TyrOH) and higher. Farnesol, 3-AT, and GA, as well as the control compound DMSO, did not inhibit cell growth at the tested concentrations.

In the serum bottle screening experiment with liquid YNB medium, TrpOH was found to have the strongest inhibitory effect on yeast cell growth at three tested concentrations in both low and high nitrogen media (FIG. 6). PheOH and TyrOH were inhibitory at 1000 mg/L in both media, but not at 40 and 200 mg/L. Boric acid appeared to have little or no growth inhibition effects at the concentrations tested.

Example 2: Small-Scale Tests of Selected Compounds on Ethanol Yield from *S. cerevisiae* JAY 270

Yeast strain: *S. cerevisiae* JAY 270, as in Example 1.
Chemicals: As in Example 1.
Procedure: Cultivations in serum bottles were used to determine the effect of the best-performing screened chemicals on the ethanol yield. *S. cerevisiae* JAY 270 was precultured in 100 mL of YPD medium in 200-mL serum bottles overnight in a shaker at 30° C. and 200 rpm. The precultured yeast cells were collected and washed twice as described above. The cell pellet was resuspended in about 10 mL of 0.8% (w/v) NaCl and the cell concentration was estimated as OD600. TyrOH, PheOH, and TrpOH were added to 30 mL of YPD medium in 100-mL serum bottles at 0.05% and 0.2% respectively. The same amount of DMSO was added to YPD medium to serve as the control for TrpOH and TyrOH treatments. The bottles were inoculated with the prepared yeast cells to obtain an initial cell concentration of OD600=0.2. The serum bottles were sealed and cultured in a shaker at 30° C. and 200 rpm for 24 h. Each condition had three biological replicates.

Analytical methods: Cell growth was evaluated by monitoring OD600 and cell dry mass concentration. For dry mass measurements, 1.0 mL of culture was transferred to a pre-dried and pre-weighed 2-mL centrifuge tube. The tubes were centrifuged for 10 min at 14000 rpm using a microcentrifuge, and then the cell pellets were dried in an oven for 3 days at 65° C. The cell dry mass was determined by subtracting the initial tube mass from the dried mass of tube with cells. The concentrations of glucose, ethanol, and glycerol were measured via HPLC (Shimadzu LC20A series) outfitted with a refractive index detector and using an Aminex HPX-87H (300×7.8 mm) organic acid column and Cation H+ guard cartridge (Bio Rad Laboratories, Hercules, CA). The column was maintained at 65° C. and the mobile phase was 5 mM sulfuric acid with a flow rate of 0.6 mL/min. Standard compound solutions were used to calibrate the HPLC. Each sample was analyzed three times by HPLC.

Results: In the qualitative screening test in 24-well plates, cycloheximide, boric acid, TyrOH, PheOH, and TrpOH reduced the growth of *S. cerevisiae* JAY 270. To determine whether these compounds can also improve the ethanol yield of *S. cerevisiae* JAY 270 during fermentation, these compounds were tested in YPD medium in serum bottles. The concentrations used were 0.05% and 0.2% (w/v) except for cycloheximide, which was tested at 0.1 and 0.4 mg/L. *S. cerevisiae* JAY 270 cells were able to grow in all the treatments except cycloheximide at 0.4 mg/L. Thus, the results of cycloheximide treatment at 0.4 mg/L are not presented. As shown in Table 2 and Table 8, the biomass yield of *S. cerevisiae* JAY 270 decreased in all treatments except boric acid at 0.05% and TyrOH at 0.05%. While the addition of cycloheximide at 0.1 mg/L resulted in a slight decrease of ethanol yield and the addition of boric acid at 0.05 and 0.2% did not affect ethanol yield. The addition of TyrOH, PheOH, and TrpOH at 0.2% increased the ethanol yield significantly. The glycerol yield decreased in all the treatments except boric acid.

The presence of PheOH, TrpOH, or TyrOH at 0.2% resulted in lower biomass and glycerol yields, and higher ethanol yields, relative to controls. These effects were more pronounced when these molecules were present at 0.2% than at 0.05%. For instance, the cell dry mass concentration was 85% of the control with 0.05% PheOH and 71% with 0.2% PheOH (Table 8). Glycerol yield reductions of more than 20% were observed after addition of PheOH, TrpOH, or TyrOH at 0.2% in the fermentation medium (Table 2). Moreover, differential effects among these molecules were noted, including that TrpOH at 0.2% (12.4 mM) had a stronger effect on growth than did 0.2% PheOH (16.4 mM) and 0.2% TyrOH (14.5 mM). Furthermore, reductions in biomass yield with PheOH, TrpOH, or TyrOH treatment were associated with increases in ethanol yield.

Example 3: Small-Scale Tests of Selected Compounds on Ethanol Yield from Different Yeast Strains Yeast strains: *S. cerevisiae* ATCC 26603 was obtained from ATCC (www.atcc.org). *S. cerevisiae* JAY 270, *S. cerevisiae* JAY 238, *S. cerevisiae* JAY 240, *S. cerevisiae* JAY 241, *S. paradoxus* JAY 1502, *S. kudriavzezii* JAY 1503, and *S. mikatae* JAY 1504 were provided by Dr. Juan Lucas Argueso at Colorado State University. All these yeast strains were maintained as frozen stocks at −80° C. Fresh cultures on yeast extract-peptone-dextrose agar (YPDA: 10 g/L yeast extract, 20 g/L peptone, 20 g/L glucose, 15 g/L agar) plates were prepared and kept at 4° C. before use.

Chemicals: As in Example 1.

Procedure: Seven yeast strains (S. cerevisiae ATCC 26603, S. cerevisiae JAY 238, S. cerevisiae JAY 240, S. cerevisiae JAY 241, S. paradoxus JAY 1502, S. kudriavzezii JAY 1503, and S. mikatae JAY 1504) were pre-cultured in 30 mL of YPD medium in 100 mL serum bottle overnight in a shaker at 30° C. and 200 rpm. The precultured yeast cells of each strains were collected and washed twice. Finally, the cell pellet was resuspended in about 10 mL 0.8% (w/v) NaCl and the OD600 measured. TyrOH, PheOH, and TrpOH were added to 30 mL of YPD medium in 100-mL serum bottles at 0.2% (w/v) respectively. The same amount of DMSO was added in YPD medium and served as control to the TrpOH and TyrOH treatments. The prepared yeast cells were added to obtain the initial cell concentration at OD600=0.2. The serum bottles were sealed and cultured in a shaker at 30° C. and 200 rpm for 24 h. There were three biological replicates for each treatment.

Analytical methods: As in Example 2.

Results: To determine whether the effects of TyrOH, PheOH, and TrpOH are similar for yeast strains other than S. cerevisiae JAY 270, seven strains of S. cerevisiae, S. paradoxus, S. kudriavzezii, and S. mikatae were grown in YPD medium with TyrOH, PheOH, and TrpOH added at 0.2% in serum bottles. Significant effects (Student's t-test, $p<0.05$) on the biomass, glycerol, and ethanol yields were observed in nearly all combinations of strains and TyrOH, PheOH, and TrpOH (Table 3 and Table 9). The addition of 0.2% TrpOH in the fermentation medium resulted in very low cell growth of S. kudriavzezii JAY 1503 and S. mikatae JAY 1504 so it was not possible to calculate the yields of cell biomass, glycerol, and ethanol in those cultivations.

TyrOH, PheOH, and TrpOH had effects on the yields of biomass, glycerol, and ethanol on seven yeast strains from the species S. cerevisiae, S. paradoxus, S. kudriavzezii, and S. mikatae (Table 3). The addition of PheOH at 0.2% led to significantly increased ethanol yield for S. cerevisiae JAY 238 and JAY 240. The addition of TyrOH and TrpOH at 0.2% led to significantly increased ethanol yield for the seven tested strains, except TrpOH with S. kudriavzezii JAY 1503 and S. mikatae JAY 1504. The effects varied in magnitude among the strains, with the most pronounced effect being a 14-15% increase from the addition of 0.2% TrpOH to S. cerevisiae strains ATCC 26603, JAY 238, JAY 240, and JAY 241. The biomass yield decreased when TyrOH, PheOH, and TrpOH were in the growth medium, except in the cases of TrpOH with S. cerevisiae JAY 241 and PheOH with S. kudriavzezii JAY 1503. The effects of TyrOH, PheOH, and TrpOH on the glycerol yield was more varied, ranging from decreases of 42% from control (TrpOH with S. cerevisiae JAY 238) to an increase of 71% (TrpOH with S. paradoxus JAY 1502).

TyrOH, PheOH, and TrpOH had different effects on these seven strains. The addition of PheOH led to an increase in ethanol yield of S. cerevisiae JAY 238 by 9.3% while the yield from S. cerevisiae JAY 241 was statistically unchanged vs. the control. The ethanol yield associated with TyrOH exposure was 10% higher S. cerevisiae JAY 240 and JAY 241, but only 5% higher in S. paradoxus JAY 1502 (Table 3). Among TyrOH, PheOH, and TrpOH, 0.2% (12.4 mM) TrpOH had the strongest effect on reducing cell growth of all tested strains in comparison to 0.2% (16.4 mM) PheOH and 0.2% (14.5 mM) TyrOH, which is consistent with the observation in S. cerevisiae JAY 270.

Example 4: Time-Course Bioreactor Studies of the Effects of PheOH and TrpOH

Yeast strain: S. cerevisiae JAY 270, as in Example 1. Inocula for bioreactor experiments with PheOH and TrpOH S. cerevisiae JAY 270 were prepared by culturing the yeast in 100 mL of YPD medium in 200-mL serum bottles overnight in a shaker at 30° C. and 200 rpm. The cells were collected by centrifuging 10 min at 4000×g and 4° C. The cell pellet was washed twice using sterile 0.8% (w/v) NaCl solution. Finally, the cell pellet was resuspended in about 15 mL of 0.8% (w/v) NaCl.

Chemicals: As in Example 1.

Procedure: Fermentations were carried out in two Eppendorf BioFlo 115 bioreactors containing 1 L sterile YNB medium with 20 g/L glucose (Difco Yeast Nitrogen Base, catalog number 239210). The prepared yeast cells were inoculated in the bioreactor vessels to obtain an initial yeast cell concentration of OD600≈0.1. The fermentation was conducted at pH 5.5, 30° C., and 200 rpm agitation. Ultrapure $N_2$ was sparged at 0.1 standard liters per minute in the bioreactor vessels to maintain anaerobic conditions. Samples were collected at different time points to monitor cell, glucose, and ethanol concentrations.

For experiments with added PheOH, 2.0 mL of PheOH stock solution was added to one of the two vessels when the OD600 reached 1.0 to achieve a final concentration of 0.2% (w/v). In the serum bottle tests, TrpOH had stronger effects on yeast cell growth than PheOH at the same tested concentration. A study in serum bottles was then conducted to determine the TrpOH concentration that would have a similar growth inhibitory effect. That test showed that TrpOH at 0.12% (w/v), or 7.5 mM, had similar growth inhibition as PheOH at 0.2% (w/v), or 16.4 mM (data not shown). Thus, for bioreactor experiments on the effects of TrpOH, the TrpOH was added at 0.12%. Since TrpOH was dissolved in DMSO, the same concentration of DMSO was added in the control bioreactor at the same time. All other bioreactor conditions were the same as in the PheOH test.

Samples were collected from the bioreactors every hour post-addition for 6 h, and again after 24 hours of cultivation. Each experiment was repeated in triplicate.

Analytical methods: As in Example 2.

Figure 2:
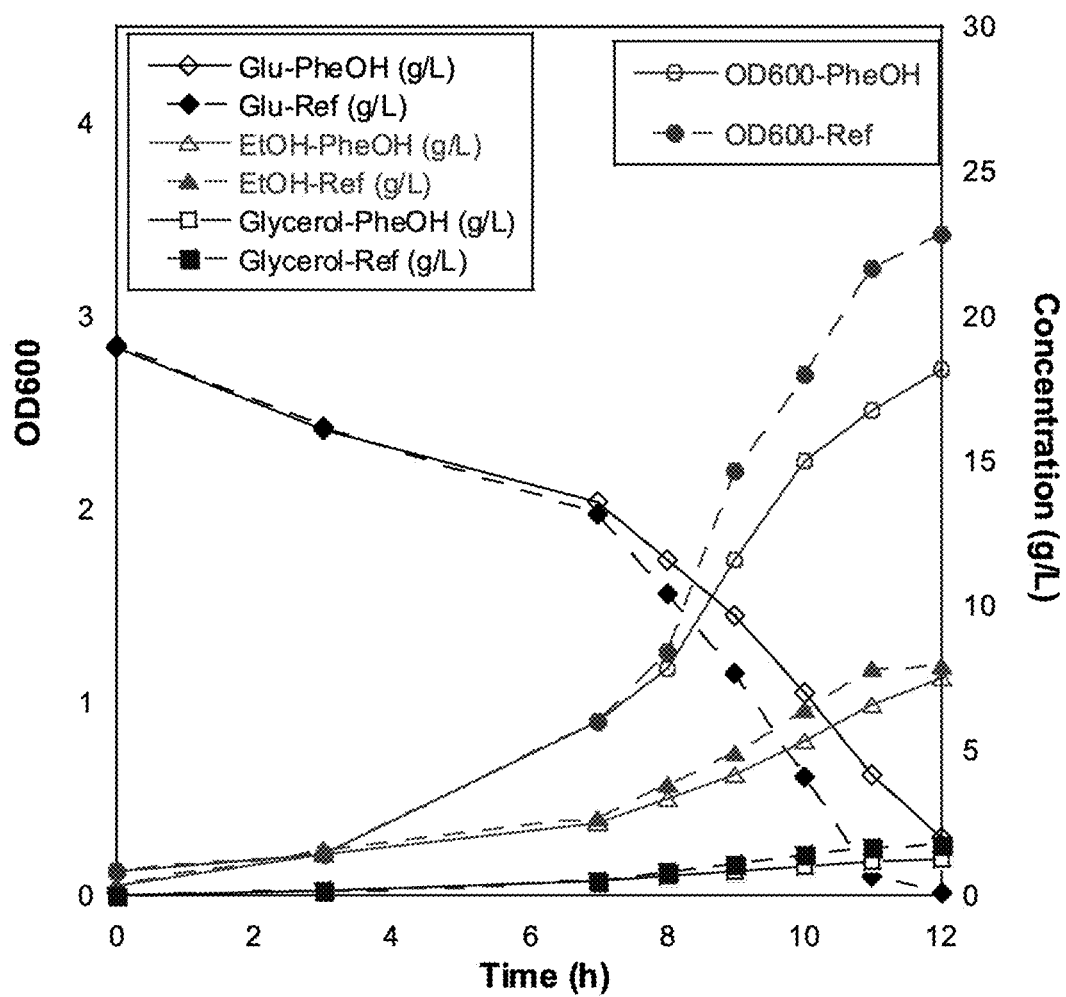
FIG. 2 is a pair of graphs (A and B) showing the results of 2-phenylethanol (PheOH) addition in 1-L bioreactors containing *S. cerevisiae* JAY 270. PheOH (final concentration 0.2% w/v) was added to the treatment bioreactor at 7 hours. This experiment was repeated in triplicate. (A): The change of glucose, ethanol, glycerol, and biomass (as OD600) concentrations during fermentation. (B): The change of ethanol, glycerol, and biomass yields after PheOH was added to the treatment bioreactor at 7 hours. The error bars are the standard deviations from 3 biological replicates.
Figure 3:
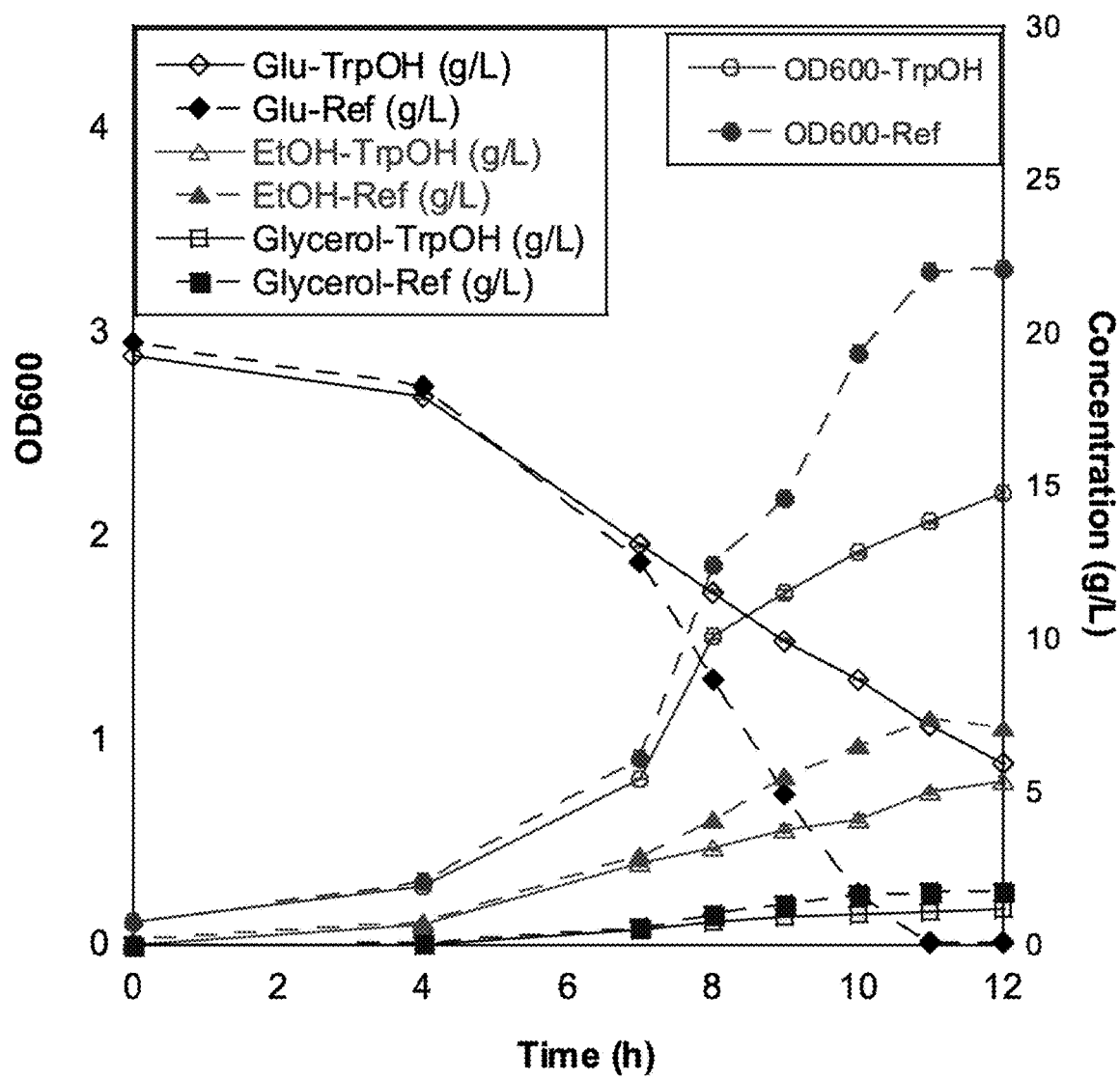

Results: In bioreactor experiments to which PheOH was added after 7 hours, PheOH slowed the fermentations (FIG. 2). The biomass, glucose, glycerol, and ethanol concentrations were similar in both bioreactors before 0.2% (w/v) PheOH was added. After that point, cell growth in the treated cultivations was slower and the final cell concentration at 24 h was 22% lower than in the control bioreactors (Table 4). The glucose in the control was completely consumed after 12 h while PheOH treatment still had about 2 g/L glucose at that time. All glucose in the PheOH-treated cultivation was consumed a few hours later. Notably, the ethanol yield was higher at all timepoints after the addition, finishing at 6% higher in the PheOH treatments than in the control cultivations (Table 4).

As in the case of PheOH, the addition of TrpOH at 0.12% resulted in slower cell growth and higher ethanol yield in comparison to the control treatment. As shown in FIG. 2, the cell, glucose, glycerol, and ethanol concentrations were similar in both bioreactors before TrpOH was added in. Thereafter, the cell growth in the treatment bioreactors was slower and the final cell concentration at 24 h was about 22% lower than that of the control bioreactor (Table 4). At that point, the glycerol concentration in TrpOH treatment was 17% lower than in the control and the ethanol yield was 10% higher in TrpOH treatment than the control.

The influence of PheOH and TrpOH on the fermentation kinetics of *S. cerevisiae* JAY 270 in YPD was evaluated in batch bioreactor experiments. The addition of 0.2% PheOH resulted in slower cell growth, glucose consumption, and ethanol production in comparison to the control (FIG. 2). Again, higher ethanol yield and lower biomass yield in comparison to the control treatment were observed (Table 4).

A non-engineered approach to increase ethanol yield via reducing biomass production is made possible by the present invention. Quorum sensing is a natural growth control system, well-studied in bacteria [Miller, M. B., & Bassler, B. L. (2001). Quorum Sensing in Bacteria. *Annual Review of Microbiology,* 55(1), 165-199.], that has been incorporated into bacterial growth control circuits using synthetic biology [Dinh, C. V., Chen, X., & Prather, K. L. J. (2020). Development of a Quorum-Sensing Based Circuit for Control of Coculture Population Composition in a Naringenin Production System. *ACS Synthetic Biology,* 9(3), 590-597.]. In *S. cerevisiae,* 2-phenylethanol, tryptophol, and tyrosol are synthesized from the amino acids phenylalanine, tryptophan, and tyrosine, respectively, through three-step biochemical reductions (transamination, decarboxylation, and reduction) via the Ehrlich pathway [Hazelwood, L. A., Daran, J. M., van Maris, A. J., Pronk, J. T., & Dickinson, J. R. (2008). The Ehrlich pathway for fusel alcohol production: a century of research on *Saccharomyces cerevisiae* metabolism. *Appl Environ Microbiol,* 74(8), 2259-2266.]. The ARO genes are responsible for the biosynthesis of, 2-phenylethanol, tryptophol and tyrosol.

Both the addition of PheOH and TrpOH in the fermentation medium resulted in about 20% lower biomass yield from *S. cerevisiae* JAY270 in comparison to that of the control treatment (FIGS. 1 and 2; Table 2). In addition, glycerol yields were decreased 15-20% by the addition of PheOH and TrpOH (FIGS. 1 and 2; Table 2). We observed that all of the added molecules (PheOH, TrpOH, or TyrOH) reduced yeast cell growth of *S. cerevisiae* at 0.2%. Further, the results show that inhibitory effects of these molecules appear to be concentration dependent (Tables 1 and 2). It was also observed that these aromatic alcohols appear to have strain- and species-specific effects (Table 3).

Strategies for increasing the ethanol yield are important for economic and environmental sustainability. Under anaerobic conditions, approximately 7% of the substrate sugar is converted into yeast biomass, resulting in substantial loss of ethanol yield [Kurylenko, O., et al. (2016). New approaches for improving the production of the 1st and 2nd generation ethanol by yeast. *Acta Biochim Pol,* 63(1), 31-38.]. The present invention provides a novel approach by using yeast growth inhibition compounds to control yeast cell growth and improve ethanol yield. Different compounds were screened for their ability to reduce cell growth of *S. cerevisiae*. It was observed that the addition PheOH, TrpOH, and TyrOH in fermentation medium resulted in decreased biomass and glycerol yields and increased ethanol yield. These findings provide a novel strategy to improve ethanol yield via the application of quorum sensing. A better understanding of the effects of these molecules on *S. cerevisiae,* such as thorough the methods and systems taught herein, will make it possible to precisely manipulate cell growth and carbon flux control during fermentation to improve the production of high value compounds.

Part II—Further Demonstrations of the Effects of Yield-Increasing Chemicals Including on Immobilized Yeast Cells One major factor in conversion efficiency is the production of cellular biomass (growth) by the microorganisms. A strategy to overcome this limitation to the conversion efficiency is to consider the flux of substrate carbon (from the fermentable components of the algal hydrolysate) to products during a bioprocess. An exemplary example disclosed herein is the fermentation (an anerobic process) of sugars in hydrolyzed algal biomass to ethanol.

In general terms, the substrate carbon is converted to ethanol, other extracellular soluble small molecule products, carbon dioxide, and biomass (FIG. 1). Increasing the conversion of substrate to ethanol means decreasing the carbon flux to the other carbon containing products. While strain engineering methods could be used for this goal, a simpler, more controllable, and faster-to implement strategy was used in which yield-increasing molecules were added to the culture medium, thereby increasing the rate of ethanol production by decreasing the rate of production of the other products. Thus, there was a reduction in the carbon flux to biomass (i.e., reduction in the growth of the yeast).

In certain aspects, the invention was exemplified using the yeast *Saccharomyces cerevisiae* strain JAY270 to produce ethanol. Three compounds were evaluated for their ability to inhibit inputs to conversion of biomass: tyrosol (TyrOH), 2-phenylethanol (PheOH), and tryptophol (TrpOH). In conjunction with this strategy, cell immobilization was used to decouple growth rate from bioreactor operation (especially important with growth-inhibited cells) and to increase the concentration of cells in the system, thereby increasing the overall bioreactor productivity.

As mentioned above, a strategy used to accomplish improvements in overall carbon conversion efficiency (CCE) was to consider the flux of substrate carbon (from the fermentable components of the algal hydrolysate) during a fermentation. In general terms, the substrate carbon is converted to ethanol, other extracellular soluble small molecule products, carbon dioxide, and biomass (FIG. 1). Increasing the conversion of substrate to ethanol necessarily means decreasing the carbon flux to the other carbon-containing products. One can think either of increasing the rate of ethanol production or decreasing the rate of production of the other products. The approach taken here was to reduce the carbon flux to biomass (i.e., reduce the growth of the yeast). While strain engineering methods could be used for this goal, a simpler, more controllable, and faster strategy was used in which growth-inhibiting molecules were added to the culture medium (actual and mock hydrolysate). Three compounds were evaluated for this purpose: tyrosol (TyrOH), 2-phenylethanol (PheOH), and tryptophol (TrpOH). In conjunction with this strategy, cell immobilization was used to decouple growth rate from bioreactor operation (especially important with growth-inhibited cells) and to increase the concentration of cells in the system, thereby increasing the overall bioreactor productivity [González, B., J. Vazquez, P. J. Cullen, A. Mas, G. Beltran and M.-J. Torij a. 2018. Aromatic Amino Acid-Derived Compounds Induce Morphological Changes and Modulate the Cell Growth of Wine Yeast Species. Front. Microbiol. doi: 10.3389/fmicb.2018.00670; Schmidt, M. D. Tran-Nguyen, and P. Chizek P. 2018. Influence of boric acid on energy metabolism and stress tolerance of *Candida albicans*. J Trace Elem Med Biol. 49, 140-145. doi: 10.1016/j.jtemb.2018.05.011.]

Example 5—Materials and Methods for Part II

Algal Biomass

The Arizona Center for Algae Technology and Innovation (AzCATI) at Arizona State University (ASU) provided *Desmodesmus armatus* SE107. The algae were grown in flat-panel PBRs using ammonium chloride as the nitrogen source and was in artificial seawater [Dong, T., E. P. Knoshaug, R. Davis, L. M. L. Laurens, S. Van Wychen, P. T. Pienkos, and N. Nagle. 2016. Combined algal processing: A novel integrated biorefinery process to produce algal biofuels and bioproducts, Algal Research 19, 316-323. doi: 10.1016/j.algal.2015.12.021]. The algal strain was harvested 5-days post nitrogen-depletion using a continuous centrifuge.

Hydrolysate and Mock Hydrolysate

*D. armatus* hydrolysate was prepared by the National Renewable Energy Laboratory ("NREL"). Owing to the relatively small amounts of hydrolysate that were available, most experiments were conducted using the standard yeast growth medium, yeast-peptone-dextrose (YPD). Previous tests at Colorado State University ("CSU") have confirmed that *S. cerevisiae* JAY270 grows faster on the *D. armatus* hydrolysate than on YPD, making YPD a conservative substitute.

Carbohydrate and Acids Analysis

Sugars and ethanol were quantified by high-performance liquid chromatography (HPLC) on an Agilent 1100/1200 HPLC system with RID detection. A Bio-Rad Aminex HPX-87H column was used with a flow rate of 0.6 mL/min using 0.01 N $H_2SO_4$ as the mobile phase. Each sample injection volume was 20 µL and the sample analysis time was 30 minutes. The column and detector temperatures were both 65° C. The HPLC was calibrated using prepared glucose standard samples in the range 0-50 g/L and ethanol samples in the range 0-20 g/L. All samples were filtered through a 0.2 µm nylon filter and diluted as necessary prior to analysis.

Yeast Immobilization Using Calcium Alginate

Sodium alginate from brown algae (Sigma 71238) was dissolved into deionized water at 4% (w/w). A flask with 150 mL 4% sodium alginate solution was autoclaved at 121° C. for 15 min and transferred into an anaerobic chamber overnight before use.

*S. cerevisiae* JAY270 cells were precultured in 600 mL YPD medium at 30° C. overnight and collected by centrifuging at 3000×g for 10 min at 4° C. The cell pellets were washed twice by resuspending in 0.8% NaCl and centrifuged to remove any medium residue. Then, the cells were resuspended in 50 mL 0.8% NaCl and mixed with the 4% sodium alginate solution to obtain the final sodium alginate concentration of 3%. The mixture was dropped with a syringe aseptically into sterilized 2% $CaCl_2 \cdot 2H_2O$ on ice to form spheres ("beads"). The cell-immobilized beads were kept in the ($CaCl_2$) solution at 4° C. until use.

Immobilized Yeast Cell Fermentation

The immobilized cells were incubated in YPD medium with 20 g/L glucose overnight at 30° C. to activate the immobilized cells. For each replicate test, 25 mL of *D. armatus* hydrolysate obtained from NREL was mixed with 15 mL beads and transferred into a 50 mL serum bottle. All serum bottles were incubated in a shaker at 150 rpm and 30° C. Samples were collected at 0, 12, and 24 h. The concentrations of sugars and ethanol in the samples were analyzed by HPLC.

Testing of Yield-Increasing Chemicals Using Immobilized Cells in Algal Hydrolysate in Serum Bottles To test the effects of yield-increasing chemicals on the immobilized cells fermentation, 0.2% PheOH or TrpOH was added in the *D. armatus* hydrolysate obtained from NREL in serum bottles respectively (batch growth). PheOH was directly added into the hydrolysate medium. TrpOH was dissolved in DMSO at 20%, then added into the hydrolysate to achieve the desired final concentration. The same amount of DMSO was added into the control cultivations. *S. cerevisiae* JAY270 cells were immobilized in calcium alginate. The immobilized cell beads were incubated in YPD medium overnight at 30° C. to activate the immobilized cells. Twenty-five mL of *D. armatus* hydrolysate was mixed with 15 mL immobilized cell beads (three biological replicates in each treatment) and incubated at 30° C. The ethanol yield was calculated at 24 hours. The content of glucose and ethanol in samples was analyzed using HPLC.

Continuous Fermentation Using Alginate-Immobilized Yeast Cells in YPD Medium

The immobilized cell reactor system consisted of two glass cylindrical columns, a vessel with agitation containing fermentation medium (controlled temperature, pH, and dissolved oxygen), and a pump for delivery of the feed to the column. The glass column had dimensions of OD=32, ID=29, and L=160 mm; screens were placed above and below the alginate bead layer to retain the cells in the column. YPD medium with 0.6 g/L $CaCl_2 \cdot 2H_2O$ was used in the continuous fermentation. Two columns (a well-mixed reactor column and a packed-bed column) were used in this test (FIG. 5). The total volume of immobilized cells used to fill the column was 80 mL and the medium volume was 20 mL in each column. The total medium volume in the system was 60 mL, including the medium in both columns and in the vessel. The flow rate of fresh medium was 2.3 mL/min.

The system was first fed with YPD medium for 20 hours to activate the immobilized cells. After 20 hours, samples were collected at different times points over 24 hours from both Column 1 (well-mixed reactor) and the entire system. Then YPD medium containing 0.2% PheOH was used to replace the YPD medium for another 26 hours. After that, the medium was changed back to YPD medium for 6 hours. The content of glucose and ethanol in samples was analyzed using HPLC.

Example 6—Effects of Yield-Increasing Chemicals on Immobilized Cells in Batch Cultivations in Algal Hydrolysate To evaluate the effects of the growth inhibitors PheOH and TrpOH on immobilized cells in *D. armatus* hydrolysates, batch cultivations in serum bottles were conducted. The sugar content of this hydrolysate was found to be 12.1 g/L glucose, 3.7 g/L mannose, and 0.5 g/L galactose. TrpOH was dissolved in DMSO, so DMSO at the appropriate concentrations was added to the control cultivations. No inhibitory effect was observed in these control cultures. Immobilized *S. cerevisiae* JAY270 completely consumed glucose and mannose but did not consume galactose to a detectable extent in this test. As shown in Table 7, the ethanol yield from immobilized cells in the control cultivations was found to be 0.45±0.01 g ethanol/g sugar at 24 hours in the control samples. This value is about 10% higher than the value reported previously of 0.41 g ethanol/g sugar for a free cell fermentation grown on a different preparation of *D. armatus* hydrolysate. Furthermore, both PheOH and TrpOH could increase the ethanol yield in comparison to their control cultivations. The addition of TrpOH at 0.2% resulted in an ethanol yield of 0.49 g ethanol/g sugar, 11.4% higher than that of the DMSO reference treatment and about 20% higher than the value for free cell fermentation of *D. armatus* hydrolysate.

Example 7—Effects of a Yield-Increasing Chemical on Immobilized Cells in Continuous Cultivations in YPD Medium To evaluate the use of the growth inhibition/yield increase strategy in a continuous cultivation, the two-column immobilized cell bioreactor system shown in FIG. 5 was used. Since the growth inhibitor slows cell growth, a continuous process would not be feasible with free cells because the chemostat would need to be very large (with very low productivity) to avoid cell washout. In contrast, cell immobilization allows the biocatalysts to be retained in the bioreactor system. The two-column system was designed to provide both high productivity and high conversion. The combination of a well-mixed bioreactor and a plug-flow bioreactor can provide higher productivities at high conversion than either bioreactor type alone.

Owing to the limited supply of algal hydrolysate, the test was conducted using YPD medium. The test was conducted with 0.2% PheOH as the growth inhibitor. For 20 hours prior to the start of the experiment, the system was fed YPD medium without PheOH to ensure that the cells were fully active following their immobilization. The experiment was then conducted with three phases:
(1) 24 hours, during which the feed was YPD medium without PheOH. The start of this phase represented time zero of the experiment.
(2) 26 hours, during which the feed was YPD medium with 0.2% PheOH.
(3) 6 hours, during which the feed was YPD medium without PheOH.

Over the course of Phase 1 (no inhibitor), the ethanol yield was 0.40-0.41 after the well-mixed reactor column (C1) and in effluent of the complete system (C1+C2) (FIG. 7). The glucose conversion was about 80% after C1 and was 98% or higher for the complete system throughout this phase. Moreover, the ethanol productivity was above 26 g/L·h in C1 and 21 g/L·h for the system.

In Phase 2, 0.2% PheOH was supplied in the medium to evaluate growth inhibition in continuous cultivation. The ethanol yield was about 0.45 and 0.43 for C1 and C1+C2, respectively, during the 26-hour test (FIG. 7). The glucose conversion was 60% after C1 and 91% for C1+C2, and the ethanol productivity was 21 g/L·h in both C1 and the whole system.

When the feeding medium was switched back to YPD medium in Phase 3, the ethanol yield returned to 0.39-0.40, similar to those in Phase 1. The glucose conversion rate was 70% and 98%, the ethanol productivity was 22 g/L·h and 20 g/L·h for C1 and the whole system respectively.

Example 8—Carbon Conversion Efficiency

The strategy of inhibiting yeast cell growth using growth inhibitors is shown herein to be successful. Of the four compounds tested that are growth-inhibitory to yeast, three were found to inhibit growth and two of these, 2-phenylethanol (PheOH) and tryptophol (TrpOH), are shown herein in several batch cultivation tests and in three media to inhibit growth while still allowing ethanol production, thereby resulting in increased ethanol yields (carbon conversion efficiencies). Notably, these effects were observed using *D. armatus* hydrolysate: in batch cultivations, the addition of 0.2% TrpOH resulted in an ethanol yield of 0.49 g ethanol/g sugar, 11.4% higher than that of the DMSO reference treatment and about 20% higher than the value for free cell fermentation of *D. armatus* hydrolysate. Increased ethanol yields were also demonstrated when 0.2% PheOH was added to the feed to an immobilized cell bioreactor. The progression in ethanol yield from the start of this project is shown in FIG. 8.

These results are significant: increases of only a few percentage points represent substantial value to the ethanol industry and enhance the life-cycle assessment of any ethanol fermentation. In addition, these findings are remarkable because ethanol has been regarded as a growth-associated product. Further investigation of the metabolic and physiological shifts associated with yeast cell exposure to these growth inhibitors can be explored. The results demonstrating increased ethanol yield not only for batch cultivation, but also for continuous cultivations with immobilized cells, are also notable. Further improvements to the techniques can include a determination of the optimal timing and level of growth inhibitor addition to achieve long-term bioreactor operation with high CCE.

The present invention provides an overall strategy for increasing CCE by limiting carbon flux to pathways other than ethanol production. As an example of that approach, a *S. cerevisae* strain modified to reduce glycerol production can be employed. This strain can be tested in several formats (e.g., immobilized, with growth inhibitors) to determine effects on CCE.

Continuous bioreactor system for high productivity and high conversion: The continuous, two-part, immobilized cell bioreactor system was shown herein to achieve both high productivity (21 g/L·h) and high glucose conversion (98%) (FIG. 7). By comparison, typical free-cell batch cultivations have an ethanol productivity of approximately 0.3 g/L·h (if the initial 20 g/L of glucose is consumed in about 24 hours to produce 8 g/L ethanol).

REFERENCES

Averianova, L. A., Balabanova, L. A., Son, O. M., Podvolotskaya, A. B., Tekutyeva, L. A. Production of Vitamin B2 (Riboflavin) by Microorganisms: An Overview. *Front. Bioeng. Biotechnol.*, 8, 1172 (2020). https://doi.org/10.3389/fbioe.2020.570828

Hallborn, J., Walfridsson, M., Airaksinen, U. et al. Xylitol Production by Recombinant *Saccharomyces cerevisiae*. *Nat Biotechnol* 9, 1090-1095 (1991). https://doi.org/10.1038/nbt1191-1090

Li, M. Kildegaard, K. R., Chen, Y., Rodriguez, A., Borodina, I., Nielsen, J. De novo production of resveratrol from glucose or ethanol by engineered *Saccharomyces cerevisiae*. Metabolic Engineering, 32, 1-11 (2015). https://doi.org/10.1016/j.ymben.2015.08.007

Li, M and Borodina, I. Application of synthetic biology for production of chemicals in yeast *Saccharomyces cerevisiae*, *FEMS Yeast Research*, 15(1), 1-12 (2015). https://doi.org/10.1111/1567-1364.12213

Novy, V., Brunner, B. & Nidetzky, B. l-Lactic acid production from glucose and xylose with engineered strains of *Saccharomyces cerevisiae*: aeration and carbon source influence yields and productivities. *Microb Cell Fact* 17, 59 (2018). https://doi.org/10.1186/s12934-018-0905-z Wu, J., Elliston, A., Le Gall, G. et al. Yeast diversity in relation to the production of fuels and chemicals. *Sci Rep* 7, 14259 (2017). https://doi.org/10.1038/s41598-017-14641-0

Glossary of Claim Terms

The embodiments of this invention are not limited to particular yeast strains or methods of improving ethanol production, which can vary as understood by skilled artisans. It is further to be understood that all terminology used herein is for the purpose of describing particular embodiments only, and is not intended to be limiting in any manner or scope.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The term "ethanol-producing microorganism" means any fermenting organism, including yeast, capable of producing ethanol from saccharides (mono- or oligo-). The term, as used herein, is synonymous with "ethanologenic microorganisms" and "fermenting organisms". A person of ordinary skill in the art can readily determine the effective amount of ethanol-producing microorganisms to be used in the methods of the present invention.

The term "fermentation" means the enzymatic and anaerobic breakdown of organic substances by microorganisms; such as the process by which sugars produce ethanol, carbon dioxide (waste product) and cellular energy. Although yeast ferments ethanol without oxygen, it is understood that the process may occur in the presence of oxygen as an aerobic process. Methods of fermentation and other ethanol-producing method steps (including separation of end products, distillation, purification and denaturation of ethanol) are well known in the art.

The term "yield" means generally the amount of end product, such as various types of ethanol (including for example fuel ethanol or industrial ethanol) produced using the methods set forth in the present invention. Yield can refer to the concentration, volume, percentage of increase, and other means of measuring end products. Most particularly, yield refers to the amount of a desired product (e.g., ethanol) that is obtained from a given amount of resource or input (e.g., substrate, sugar, glucose); expressed as a ratio of concentration or masses. Thus, yield provides a measure of efficiency. The preferred end product measured with the invention is an alcohol product, preferably ethanol, which may be separated and/or purified according to methods known to those of ordinary skill in the art.

"Analog" or "analogue" as used herein, refers to a chemical compound that possesses similar or identical activity or function(s) as the chemical having the desired activity and growth inhibitory effect of the present invention (e.g., to inhibit biomass production from the carbon substrate/sugar source), but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or other small molecules that are prepared either synthetically or isolated from a natural source, such as a plant, that retain at least one function of the active parent molecule but may be structurally different. Chemical modifications may include, for example, replacement of hydrogen by an alkyl, hydroxyl, or carboxyl group. It may also refer to chemically similar compounds which have been chemically altered to increase bioavailability, absorption, or to decrease toxicity.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE 1

Screening of *S. cerevisiae* JAY 270 growth in 24-well plates on YPDA with addition of potential growth inhibitory compounds at different concentrations at 30° C. for 24 h. Cell growth was evaluated by visual observation of the colony size in the well and scored as 0, +, ++, and +++. A score of "0" indicates no cell growth in the well and "+++" means the treatment had a colony size similar to the reference. DMSO was the reference for TrpOH and TyrOH.

| Compounds | Concentration (w/v) | | | | |
|---|---|---|---|---|---|
| | 0.00% | 0.03% | 0.05% | 0.10% | 0.20% |
| DMSO | +++ | +++ | +++ | +++ | +++ |
| PheOH | +++ | +++ | +++ | ++ | + |
| TrpOH | +++ | +++ | ++ | + | 0 |
| TyrOH | +++ | +++ | +++ | +++ | + |
| Farnesol | +++ | +++ | +++ | +++ | +++ |
| Boric acid | +++ | +++ | +++ | ++ | + |
| 3-amino-1,2,4-triazole | +++ | +++ | +++ | +++ | +++ |
| Cycloheximide | +++ | 0 | 0 | 0 | 0 |
| Glufosinate ammonium | +++ | +++ | +++ | +++ | +++ |

TABLE 2

Effects of cycloheximide (CH), boric acid (BA), tyrosol (TyrOH), 2-phenylethanol (PheOH), and tryptophol (TrpOH) on biomass, glycerol, and ethanol yields of *S. cerevisiae* JAY 270 in serum bottles. TrpOH and TyrOH tests used YPD + DMSO as control. The mean and standard deviations from three biological replicates are presented. An asterisk indicates differences at $p < 0.05$ as determined by the Student's t-test between a treatment and its control.

| Conditions | Biomass yield (g/g) | % change vs. control | Glycerol yield (g/g) | % change vs. control | EtOH yield (g/g) | % change vs. control |
|---|---|---|---|---|---|---|
| CH (0.1 mg/L) | 0.084 + 0.002 | −12* | 0.025 + 0.001 | −48* | 0.42 + 0.01 | −3.5 |
| BA-0.2% (w/v) | 0.116 + 0.001 | −15* | 0.027 + 0.001 | 6.9 | 0.41 + 0.01 | 0 |
| BA-0.05% (w/v) | 0.137 + 0.001 | 0 | 0.024 + 0.001 | 0 | 0.41 + 0.00 | 0 |
| PheOH-0.2% (w/v) | 0.064 + 0.002 | −35* | 0.025 + 0.001 | −25* | 0.41 + 0.01 | 6.2* |
| PheOH-0.05% (w/v) | 0.088 + 0.001 | −11* | 0.031 + 0.001 | −4.6 | 0.40 + 0.00 | 3.7 |
| TrpOH-0.2% (w/v) | 0.042 + 0.006 | −58* | 0.027 + 0.009 | −22* | 0.41 + 0.01 | 10* |
| TrpOH-0.05% (w/v) | 0.078 + 0.001 | −22* | 0.027 + 0.001 | −20* | 0.41 + 0.01 | 7.9* |
| TyrOH-0.2% (w/v) | 0.085 + 0.003 | −15* | 0.027 + 0.000 | −20* | 0.40 + 0.00 | 6.9* |
| TyrOH-0.05% (w/v) | 0.095 + 0.001 | −5 | 0.031 + 0.001 | −9 | 0.38 + 0.01 | 0.8 |

TABLE 3A

Effects of tyrosol (TyrOH), 2-phenylethanol (PheOH), tryptophol (TrpOH) on biomass yield from seven yeast strains.

| Strain | Condition | Biomass Yield (g/g) | % change vs. control |
|---|---|---|---|
| *S. cerevisiae* ATCC 26603 | PheOH (0.2%) | 0.052 ± 0.001 | −22* |
| | TrpOH (0.2%) | 0.059 ± 0.001 | −17* |
| | TyrOH (0.2%) | 0.056 ± 0.003 | −21* |
| | Control | 0.066 ± 0.001 | |
| | DMSO control | 0.071 ± 0.003 | |
| *S. cerevisiae* JAY 238 | PheOH (0.2%) | 0.059 ± 0.000 | −19* |
| | TrpOH (0.2%) | 0.060 ± 0.000 | −12* |
| | TyrOH (0.2%) | 0.058 ± 0.001 | −14* |
| | Control | 0.072 ± 0.001 | |
| | DMSO control | 0.068 ± 0.001 | |
| *S. cerevisiae* JAY 240 | PheOH (0.2%) | 0.060 ± 0.000 | −19* |
| | TrpOH (0.2%) | 0.055 ± 0.006 | −24* |
| | TyrOH (0.2%) | 0.061 ± 0.002 | −16* |
| | Control | 0.075 ± 0.002 | |
| | DMSO control | 0.072 ± 0.003 | |
| *S. cerevisiae* JAY 241 | PheOH (0.2%) | 0.042 ± 0.001 | −28* |
| | TrpOH (0.2%) | 0.063 ± 0.004 | +8.6 |
| | TyrOH (0.2%) | 0.049 ± 0.000 | −16* |
| | Control | 0.059 ± 0.002 | |
| | DMSO control | 0.058 ± 0.004 | |
| *S. paradoxus* JAY 1502 | PheOH (0.2%) | 0.048 ± 0.001 | −30* |
| | TrpOH (0.2%) | 0.038 ± 0.001 | −42* |
| | TyrOH (0.2%) | 0.055 ± 0.000 | −15* |
| | Control | 0.068 ± 0.001 | |
| | DMSO control | 0.065 ± 0.002 | |
| *S. kudriavzezii* JAY 1503 | PheOH (0.2%) | 0.036 ± 0.001 | −19 |
| | TrpOH (0.2%) | NA | |
| | TyrOH (0.2%) | 0.029 ± 0.000 | −35* |
| | Control | 0.043 ± 0.004 | |
| | DMSO control | 0.044 ± 0.007 | |
| *S. mikatae* JAY 1504 | PheOH (0.2%) | 0.053 ± 0.000 | −14 |
| | TrpOH (0.2%) | NA | |
| | TyrOH (0.2%) | 0.052 ± 0.000 | −20* |
| | Control | 0.062 ± 0.001 | |
| | DMSO control | 0.065 ± 0.001 | |

For Tables 3A-3C the mean values and standard deviations from three replicates were presented. Student's t-test (p<0.05) was carried out to compare the statistical difference between treatment and control. "NA" means there was no data because of extremely low cell growth.

TABLE 3B

Effects of tyrosol (TyrOH), 2-phenylethanol (PheOH), tryptophol (TrpOH) on glycerol yield from seven yeast strains.

| Strain | Condition | Glycerol Yield (g/g) | % change vs. control |
|---|---|---|---|
| S. cerevisiae ATCC 26603 | PheOH (0.2%) | 0.054 ± 0.001 | −25* |
| | TrpOH (0.2%) | 0.054 ± 0.005 | −25* |
| | TyrOH (0.2%) | 0.064 ± 0.006 | −12* |
| | Control | 0.071 ± 0.003 | |
| | DMSO control | 0.072 ± 0.002 | |
| S. cerevisiae JAY 238 | PheOH (0.2%) | 0.041 ± 0.002 | −0.2 |
| | TrpOH (0.2%) | 0.023 ± 0.002 | −49* |
| | TyrOH (0.2%) | 0.036 ± 0.002 | −8.3 |
| | Control | 0.041 ± 0.000 | |
| | DMSO control | 0.039 ± 0.000 | |
| S. cerevisiae JAY 240 | PheOH (0.2%) | 0.038 ± 0.002 | +2.2 |
| | TrpOH (0.2%) | 0.035 ± 0.000 | −12* |
| | TyrOH (0.2%) | 0.034 ± 0.001 | −15* |
| | Control | 0.038 ± 0.000 | |
| | DMSO control | 0.040 ± 0.000 | |
| S. cerevisiae JAY 241 | PheOH (0.2%) | 0.037 ± 0.002 | −31* |
| | TrpOH (0.2%) | 0.041 ± 0.004 | −26* |
| | TyrOH (0.2%) | 0.043 ± 0.000 | −23* |
| | Control | 0.054 ± 0.000 | |
| | DMSO control | 0.056 ± 0.001 | |
| S. paradoxus JAY 1502 | PheOH (0.2%) | 0.048 ± 0.002 | +22* |
| | TrpOH (0.2%) | NA | |
| | TyrOH (0.2%) | 0.041 ± 0.001 | −9.9 |
| | Control | 0.039 ± 0.001 | |
| | DMSO control | 0.045 ± 0.001 | |
| S. kudriavzezii JAY 1503 | PheOH (0.2%) | 0.060 ± 0.005 | +19* |
| | TrpOH (0.2%) | NA | |
| | TyrOH (0.2%) | 0.056 ± 0.001 | +8.1 |
| | Control | 0.050 ± 0.001 | |
| | DMSO control | 0.052 ± 0.004 | |
| S. mikatae JAY 1504 | PheOH (0.2%) | 0.043 ± 0.007 | +4.1 |
| | TrpOH (0.2%) | NA | |
| | TyrOH (0.2%) | 0.036 ± 0.001 | −24* |
| | Control | 0.041 ± 0.000 | |
| | DMSO control | 0.047 ± 0.001 | |

TABLE 3C

Effects of tyrosol (TyrOH), 2-phenylethanol (PheOH), tryptophol (TrpOH) on ethanol yield from seven yeast strains.

| Strain | Condition | EtOH Yield (g/g) | % change vs. control |
|---|---|---|---|
| S. cerevisiae ATCC 26603 | PheOH (0.2%) | 0.453 ± 0.006 | +1.2 |
| | TrpOH (0.2%) | 0.495 ± 0.008 | +14* |
| | TyrOH (0.2%) | 0.467 ± 0.015 | +7.7* |
| | Control | 0.460 ± 0.009 | |
| | DMSO control | 0.433 ± 0.026 | |
| S. cerevisiae JAY 238 | PheOH (0.2%) | 0.472 ± 0.017 | +9.3* |
| | TrpOH (0.2%) | 0.482 ± 0.017 | +15* |
| | TyrOH (0.2%) | 0.455 ± 0.016 | +8.3* |
| | Control | 0.432 ± 0.006 | |
| | DMSO control | 0.420 ± 0.003 | |
| S. cerevisiae JAY 240 | PheOH (0.2%) | 0.448 ± 0.018 | +8.2* |
| | TrpOH (0.2%) | 0.464 ± 0.053 | +15* |
| | TyrOH (0.2%) | 0.446 ± 0.022 | +10* |
| | Control | 0.414 ± 0.007 | |
| | DMSO control | 0.405 ± 0.001 | |
| S. cerevisiae JAY 241 | PheOH (0.2%) | 0.399 ± 0.003 | +0.4 |
| | TrpOH (0.2%) | 0.435 ± 0.035 | +14* |
| | TyrOH (0.2%) | 0.422 ± 0.013 | +10* |
| | Control | 0.398 ± 0.002 | |
| | DMSO control | 0.382 ± 0.002 | |
| S. paradoxus JAY 1502 | PheOH (0.2%) | 0.393 ± 0.000 | +2.7 |
| | TrpOH (0.2%) | 0.417 ± 0.056 | +7.2* |
| | TyrOH (0.2%) | 0.410 ± 0.014 | +5.4* |
| | Control | 0.383 ± 0.010 | |
| | DMSO control | 0.389 ± 0.011 | |
| S. kudriavzezii JAY 1503 | PheOH (0.2%) | 0.399 ± 0.030 | +8.7 |
| | TrpOH (0.2%) | NA | |
| | TyrOH (0.2%) | 0.388 ± 0.000 | +7.8* |
| | Control | 0.367 ± 0.002 | |
| | DMSO control | 0.360 ± 0.010 | |
| S. mikatae JAY 1504 | PheOH (0.2%) | 0.386 ± 0.009 | +3.6 |
| | TrpOH (0.2%) | NA | |
| | TyrOH (0.2%) | 0.359 ± 0.042 | +6.7* |
| | Control | 0.373 ± 0.005 | |
| | DMSO control | 0.336 ± 0.005 | |

TABLE 4

Summary of yields from cultivations treated with TrpOH (0.12% w/v) and PheOH (0.2% w/v) vs. their reference cultivations in 1-L bioreactors at 24 hours. Mean and standard deviations are calculated from triplicate experiments. An asterisk (*) indicates a difference between treatment and control at $p < 0.05$ as determined by the Student's t-test.

| Tests | Biomass yield (g/g) | % change vs. control | Glycerol yield (g/g) | % change vs. control | EtOH yield (g/g) | % change vs. control |
|---|---|---|---|---|---|---|
| PheOH-Control | 0.082 ± 0.012 | | 0.088 ± 0.001 | | 0.413 ± 0.004 | |
| PheOH-0.2% (w/v) | 0.063 ± 0.008 | −23 ± 5* | 0.071 ± 0.001 | −20 ± 2* | 0.435 ± 0.003 | 5.3 ± 0.8* |
| TrpOH-Control | 0.087 ± 0.007 | | 0.085 ± 0.005 | | 0.394 ± 0.010 | |
| TrpOH-0.12% (w/v) | 0.063 ± 0.008 | −28 ± 5* | 0.070 ± 0.004 | −17 ± 2* | 0.420 ± 0.012 | 6.5 ± 3.1* |

TABLE 5

Effects of PheOH on yeast growth and ethanol yield in serum bottles.

| | OD600 at 0 h | OD600 at 26 h | EtOH yield (g/g) | EtOH yield % Δ from control |
|---|---|---|---|---|
| Low cell inoculum | | | | |
| PheOH-0.05% | 0.70 | 3.28 | 0.47 | −1.9 |
| PheOH-0.1% | 0.70 | 2.83 | 0.45 | −4.6 |
| PheOH-0.2% | 0.70 | 2.41 | 0.47 | −1.1 |
| High cell inoculum | | | | |
| PheOH-0.05% | 1.96 | 4.24 | 0.47 | 3.1 |
| PheOH-0.1% | 1.96 | 3.99 | 0.47 | 1.7 |
| PheOH-0.2% | 1.96 | 3.53 | 0.48 | 4.9 |

TABLE 6

Effects of TrpOH on yeast growth and ethanol yield in serum bottles.

| | OD600 at 0 h | OD600 at 48 h | EtOH yield (g/g) | EtOH yield % Δ from control |
|---|---|---|---|---|
| Low cell inoculum | | | | |
| TrpOH-0.05% | 0.30 | 1.17 | 0.50 | 5.7 |
| TrpOH-0.1% | 0.30 | 0.79 | 0.50 | 2.2 |
| TrpOH-0.2% | 0.30 | 0.51 | 0.52 | 5.9 |
| High cell inoculum | | | | |
| TrpOH-0.05% | 0.85 | 2.47 | 0.52 | 4.6 |
| TrpOH-0.1% | 0.85 | 1.87 | 0.54 | 7.6 |
| TrpOH-0.2% | 0.85 | 1.40 | 0.51 | 1.9 |

TABLE 7

Effects of PheOH and TrpOH on ethanol yield of immobilized yeast cells in triplicate batch cultivations on *D. armatus* hydrolysate.

| | EtOH yield (g/g) | Standard deviation | EtOH yield % Δ from control |
|---|---|---|---|
| Control | 0.45 | 0.01 | |
| PheOH-0.2% | 0.46 | 0.01 | 1.54 |
| DMSO-Control | 0.44 | 0.03 | |
| TrpOH-0.2% | 0.49 | 0.00 | 11.42 |

TABLE 8

Effects of chemical additions on cultivations of *S. cerevisiae* JAY 270 grown in YPD medium in serum bottles. NG: negligible growth, DMSO: dimethyl sulfoxide, PheOH: 2-phenylethanol, TrpOH: tryptophol, TyrOH: tyrosol, CH: cycloheximide, BA: boric acid.

| | OD600 | SD | Biomass yield (mg/g) | Biomass yield vs. reference (%) | Glycerol yield (g/g) | Glycerol yield vs. reference (%) | Ethanol yield (g/g) | Ethanol yield vs. reference (%) |
|---|---|---|---|---|---|---|---|---|
| Reference | 3.77 | 0.06 | 0.098 + 0.001 | | 0.033 + 0.001 | | 0.39 + 0.01 | |
| PheOH-0.2% | 2.44 | 0.08 | 0.064 + 0.002 | −35.3 | 0.025 + 0.001 | −25.1 | 0.41 + 0.01 | 6.2 |
| PheOH-0.05% | 3.35 | 0.05 | 0.088 + 0.001 | −10.8 | 0.031 + 0.001 | −4.6 | 0.40 + 0.00 | 3.7 |
| DMSO-reference 0.2% | 3.86 | 0.10 | 0.101 + 0.003 | | 0.034 + 0.000 | | 0.37 + 0.01 | |
| DMSO-reference 0.05% | 3.85 | 0.05 | 0.100 + 0.001 | | 0.034 + 0.001 | | 0.38 + 0.00 | |
| TrpOH-0.2% | 1.52 | 0.12 | 0.042 + 0.006 | −58.2 | 0.027 + 0.009 | −21.9 | 0.41 + 0.01 | 10.3 |
| TrpOH-0.05% | 3.01 | 0.04 | 0.078 + 0.001 | −22.0 | 0.027 + 0.001 | −19.6 | 0.41 + 0.01 | 7.9 |
| TyrOH-0.2% | 3.27 | 0.12 | 0.085 + 0.003 | −15.3 | 0.027 + 0.000 | −19.9 | 0.40 + 0.00 | 6.9 |
| TyrOH-0.05% | 3.66 | 0.02 | 0.095 + 0.001 | −5.0 | 0.031 + 0.001 | −9.0 | 0.38 + 0.01 | 0.8 |
| Reference | 4.89 | 0.02 | 0.131 + 0.001 | | 0.047 + 0.000 | | 0.42 + 0.01 | |
| CH-0.4 mg/L | 0.22 | 0.01 | NG | NG | NG | NG | NG | NG |
| CH-0.1 mg/L | 2.82 | 0.06 | 0.084 + 0.002 | −36.1 | 0.065 + 0.002 | 0.4 | 0.42 + 0.01 | 0 |
| Reference | 4.79 | 0.02 | 0.137 + 0.001 | | 0.025 + 0.001 | | 0.41 + 0.00 | |
| BA-0.2% | 3.96 | 0.02 | 0.114 + 0.001 | −15.3 | 0.027 + 0.000 | 6.9 | 0.41 + 0.00 | 0 |
| BA-0.05% | 4.78 | 0.02 | 0.137 + 0.001 | 0 | 0.024 + 0.001 | −6.3 | 0.41 + 0.00 | 0 |

TABLE 9A

Effects of chemical additions on cultivations seven yeast strains grown in YPD medium in serum bottles. Δ: change, Ref: reference, DCW: dry cell weight, DMSO: dimethyl sulfoxide, PheOH: 2-phenylethanol, TrpOH: tryptophol, TyrOH: tyrosol.

| Strain | | OD600 | OD600 SD | Δ vs. ref (%) | DCW (mg) | DCW SD | Δ vs. ref (%) |
|---|---|---|---|---|---|---|---|
| *S. cerevisiae* ATCC 26603 | PheOH (0.2%) | 1.27 | 0.02 | 85.6 | 1.40 | 0.16 | 76.4 |
| | TrpOH (0.2%) | 0.77 | 0.01 | 54.8 | 1.13 | 0.12 | 64.2 |
| | TyrOH (0.2%) | 1.34 | 0.05 | 95.5 | 1.53 | 0.21 | 86.8 |
| | Ref | 1.48 | 0.12 | | 1.83 | 0.17 | |
| | Ref-DMSO | 1.40 | 0.04 | | 1.77 | 0.05 | |
| *S. cerevisiae* JAY 238 | PheOH (0.2%) | 1.64 | 0.03 | 65.9 | 2.00 | 0.14 | 78.4 |
| | TrpOH (0.2%) | 0.39 | 0.01 | 16.7 | 1.30 | 0.07 | 46.4 |
| | TyrOH (0.2%) | 1.99 | 0.03 | 85.0 | 2.35 | 0.11 | 83.9 |
| | Ref | 2.49 | 0.05 | | 2.55 | 0.11 | |
| | Ref-DMSO | 2.34 | 0.02 | | 2.80 | 0.07 | |
| *S. cerevisiae* JAY 240 | PheOH (0.2%) | 1.89 | 0.02 | 72.2 | 2.20 | 0.29 | 78.6 |
| | TrpOH (0.2%) | 1.12 | 0.03 | 45.0 | 1.55 | 0.11 | 50.8 |
| | TyrOH (0.2%) | 2.09 | 0.08 | 83.9 | 2.65 | 0.11 | 86.9 |
| | Ref | 2.62 | 0.10 | | 2.80 | 0.16 | |
| | Ref-DMSO | 2.49 | 0.12 | | 3.05 | 0.05 | |

TABLE 9A-continued

Effects of chemical additions on cultivations seven yeast strains grown in YPD medium in serum bottles. Δ: change, Ref: reference, DCW: dry cell weight, DMSO: dimethyl sulfoxide, PheOH: 2-phenylethanol, TrpOH: tryptophol, TyrOH: tyrosol.

| Strain | | OD600 | OD600 SD | Δ vs. ref (%) | DCW (mg) | DCW SD | Δ vs. ref (%) |
|---|---|---|---|---|---|---|---|
| S. cerevisiae JAY 241 | PheOH (0.2%) | 1.45 | 0.04 | 69.9 | 2.10 | 0.07 | 80.8 |
| | TrpOH (0.2%) | 1.00 | 0.17 | 50.1 | 1.55 | 0.11 | 58.5 |
| | TyrOH (0.2%) | 1.68 | 0.01 | 84.0 | 2.35 | 0.11 | 88.7 |
| | Ref | 2.08 | 0.10 | | 2.60 | 0.07 | |
| | Ref-DMSO | 2.00 | 0.15 | | 2.65 | 0.11 | |
| S. paradoxus JAY 1502 | PheOH (0.2%) | 1.64 | 0.03 | 70.0 | 1.95 | 0.11 | 78.0 |
| | TrpOH (0.2%) | 0.40 | 0.02 | 18.0 | 1.40 | 0.07 | 52.8 |
| | TyrOH (0.2%) | 1.90 | 0.03 | 85.5 | 2.15 | 0.11 | 81.1 |
| | Ref | 2.34 | 0.02 | | 2.50 | 0.07 | |
| | Ref-DMSO | 2.23 | 0.07 | | 2.65 | 0.11 | |
| S. kudriavzezii JAY 1503 | PheOH (0.2%) | 0.92 | 0.09 | 74.9 | 1.90 | 0.07 | 84.4 |
| | TrpOH (0.2%) | 0.16 | 0.00 | 9.9 | 0.48 | 0.13 | 18.6 |
| | TyrOH (0.2%) | 0.82 | 0.01 | 52.4 | 2.10 | 0.07 | 82.4 |
| | Ref | 1.22 | 0.03 | | 2.25 | 0.05 | |
| | Ref-DMSO | 1.57 | 0.37 | | 2.55 | 0.11 | |
| S. mikatae JAY 1504 | PheOH (0.2%) | 1.85 | 0.07 | 82.9 | 2.35 | 0.11 | 77.1 |
| | TrpOH (0.2%) | 0.64 | 0.01 | 28.1 | 1.45 | 0.11 | 43.3 |
| | TyrOH (0.2%) | 1.75 | 0.04 | 77.3 | 2.65 | 0.11 | 79.1 |
| | Ref | 2.23 | 0.03 | | 3.05 | 0.05 | |
| | Ref-DMSO | 2.26 | 0.05 | | 3.35 | 0.11 | |

TABLE 9B

Effects of chemical additions on cultivations seven yeast strains grown in YPD medium in serum bottles. Δ: change, Ref: reference, DCW: dry cell weight, DMSO: dimethyl sulfoxide, PheOH: 2-phenylethanol, TrpOH: tryptophol, TyrOH: tyrosol.

| Strain | | Biomass Yield (g/g) | Δ vs. ref (%) | Glycerol yield (g/g) | Δ vs. ref (%) | Ethanol yield (g/g) | Δ vs. ref (%) |
|---|---|---|---|---|---|---|---|
| S. cerevisiae ATCC 26603 | PheOH (0.2%) | 0.052 + 0.001 | −22.3 | 0.054 + 0.001 | −25.07 | 0.453 + 0.006 | 1.2 |
| | TrpOH (0.2%) | 0.059 + 0.001 | −16.7 | 0.054 + 0.005 | −24.74 | 0.495 + 0.008 | 14.2 |
| | TyrOH (0.2%) | 0.056 + 0.003 | −20.6 | 0.064 + 0.006 | −11.82 | 0.467 + 0.015 | 7.7 |
| | Ref | 0.066 + 0.001 | | 0.071 + 0.003 | | 0.460 + 0.009 | |
| | Ref-DMSO | 0.071 + 0.003 | | 0.072 + 0.002 | | 0.433 + 0.026 | |
| S. cerevisiae JAY 238 | PheOH (0.2%) | 0.059 + 0.000 | −18.9 | 0.041 + 0.002 | −0.22 | 0.472 + 0.017 | 9.3 |
| | TrpOH (0.2%) | 0.060 + 0.000 | −11.8 | 0.020 + 0.002 | −48.90 | 0.482 + 0.017 | 14.7 |
| | TyrOH (0.2%) | 0.058 + 0.001 | −13.9 | 0.036 + 0.002 | −8.30 | 0.455 + 0.016 | 8.3 |
| | Ref | 0.072 + 0.001 | | 0.041 + 0.000 | | 0.432 + 0.006 | |
| | Ref-DMSO | 0.068 + 0.001 | | 0.039 + 0.000 | | 0.420 + 0.003 | |
| S. cerevisiae JAY 240 | PheOH (0.2%) | 0.060 + 0.000 | −19.1 | 0.038 + 0.002 | 2.20 | 0.448 + 0.018 | 8.2 |
| | TrpOH (0.2%) | 0.055 + 0.006 | −23.5 | 0.035 + 0.000 | −11.63 | 0.464 + 0.053 | 14.5 |
| | TyrOH (0.2%) | 0.061 + 0.002 | −15.7 | 0.034 + 0.001 | −14.77 | 0.446 + 0.022 | 10.1 |
| | Ref | 0.075 + 0.002 | | 0.038 + 0.000 | | 0.414 + 0.007 | |
| | Ref-DMSO | 0.072 + 0.003 | | 0.040 + 0.000 | | 0.405 + 0.001 | |
| S. cerevisiae JAY 241 | PheOH (0.2%) | 0.042 + 0.001 | −27.9 | 0.037 + 0.002 | −31.00 | 0.399 + 0.003 | 0.4 |
| | TrpOH (0.2%) | 0.063 + 0.004 | 8.6 | 0.041 + 0.004 | −25.72 | 0.435 + 0.035 | 13.8 |
| | TyrOH (0.2%) | 0.049 + 0.000 | −15.7 | 0.043 + 0.000 | −23.39 | 0.422 + 0.013 | 10.4 |
| | Ref | 0.059 + 0.002 | | 0.054 + 0.000 | | 0.398 + 0.002 | |
| | Ref-DMSO | 0.058 + 0.004 | | 0.056 + 0.001 | | 0.382 + 0.002 | |
| S. paradoxus JAY 1502 | PheOH (0.2%) | 0.048 + 0.001 | −29.8 | 0.048 + 0.002 | 21.98 | 0.393 + 0.000 | 2.7 |
| | TrpOH (0.2%) | 0.038 + 0.001 | −42.0 | NA | | 0.417 + 0.056 | 7.2 |
| | TyrOH (0.2%) | 0.055 + 0.000 | −15.4 | 0.041 + 0.001 | −9.89 | 0.410 + 0.014 | 5.4 |
| | Ref | 0.068 + 0.001 | | 0.039 + 0.001 | | 0.383 + 0.010 | |
| | Ref-DMSO | 0.065 + 0.002 | | 0.045 + 0.001 | | 0.389 + 0.011 | |
| S. kudriavzezii JAY 1503 | PheOH (0.2%) | 0.043 + 0.004 | 18.6 | 0.06 + 0.005 | 18.78 | 0.399 + 0.030 | 8.7 |
| | TrpOH (0.2%) | NA | | NA | | NA | |
| | TyrOH (0.2%) | 0.029 + 0.000 | −35.1 | 0.056 + 0.001 | 8.07 | 0.388 + 0.000 | 7.8 |
| | Ref | 0.036 + 0.001 | | 0.05 + 0.001 | | 0.367 + 0.002 | |
| | Ref-DMSO | 0.044 + 0.007 | | 0.052 + 0.004 | | 0.360 + 0.010 | |
| S. mikatae JAY 1504 | PheOH (0.2%) | 0.053 + 0.000 | −13.8 | 0.043 + 0.007 | 4.09 | 0.386 + 0.009 | 3.6 |
| | TrpOH (0.2%) | NA | | NA | | NA | |
| | TyrOH (0.2%) | 0.052 + 0.000 | −20.1 | 0.036 + 0.001 | −23.65 | 0.359 + 0.042 | 6.7 |
| | Ref | 0.062 + 0.001 | | 0.041 + 0.000 | | 0.373 + 0.005 | |
| | Ref-DMSO | 0.065 + 0.001 | | 0.047 + 0.001 | | 0.336 + 0.005 | |

What is claimed is:

1. A method for the increased conversion of an organic substrate to a fermentation product comprising the steps of:
providing a population of yeast cells;
fermenting the organic substrate with the yeast cells in a solution comprising a compound selected from the group consisting of tyrosol (TyrOH), 2-phenylethanol (PheOH), tryptophol (TrpOH), and combinations thereof; and
collecting the resultant fermentation product from the fermentation.

2. The method for the increased conversion of an organic substrate to a fermentation product according to claim 1 wherein the yeast cells are immobilized prior to the fermentation process.

3. The method for the increased conversion of an organic substrate to a fermentation product according to claim 1 wherein the yeast cells are a yeast cell from the genus *Saccharomyces*.

4. The method for the increased conversion of an organic substrate to a fermentation product according to claim 1 wherein the yeast cell is selected from the group consisting of *S. cerevisiae, S. paradoxus, S. kudriavzezii,* and *S. mikatae*.

5. The method for the increased conversion of an organic substrate to a fermentation product according to claim 1 wherein the yeast cell is *Saccharomyces cerevisiae*.

6. The method for the increased conversion of an organic substrate to a fermentation product according to claim 1 wherein the organic substrate is a fermentable sugar.

7. The method for the increased conversion of an organic substrate to a fermentation product according to claim 1 wherein the fermentation product is a product selected from the group consisting of ethanol, lactic acid, riboflavin, ethyl acetate, arabinitol, glycerol, xylitol, or resveratrol.

8. The method of for enhancing the conversion of sugar to ethanol according to claim 1 wherein the yield increasing compound is tyrosol (TyrOH), 2-phenylethanol (PheOH), or tryptophol (TrpOH) at a concentration of about 0.05% to about 0.3%.

9. The method of for enhancing the conversion of sugar to ethanol according to claim 1 wherein the compound is tyrosol (TyrOH), 2-phenylethanol (PheOH), or tryptophol (TrpOH) at a concentration in excess of 0.1%.

10. A method for the increased conversion of a fermentable sugar to ethanol comprising the steps of:
providing a *S. cerevisiae* strain;
fermenting the sugar with the *S. cerevisiae* strain cells in a solution comprising a compound selected from the group consisting of tyrosol (TyrOH), 2-phenylethanol (PheOH), tryptophol (TrpOH), and combinations thereof; and
collecting the resultant ethanol from the fermentation.

11. The method for the increased conversion of a fermentable sugar to ethanol according to claim 10 wherein the compound is at a concentration of greater than 0.10%.

12. The method for the increased conversion of a fermentable sugar to ethanol according to claim 10 wherein the compound is at a concentration of about 0.20% to about 0.50%.

13. The method for the increased conversion of a fermentable sugar to ethanol according to claim 10 wherein the compound is at a concentration of about 0.12% to about 0.25%.

14. The method for the increased conversion of a fermentable sugar to ethanol according to claim 10 further comprising the step of immobilizing the *S. cerevisiae* strain in calcium alginate prior to the fermenting step.

* * * * *